(12) United States Patent
Conte et al.

(10) Patent No.: US 7,745,477 B2
(45) Date of Patent: Jun. 29, 2010

(54) HETEROARYL AND BENZYL AMIDE COMPOUNDS

(75) Inventors: Aurelia Conte, Basel (CH); Holger Kuehne, Grenzach-Wyhlen (DE); Thomas Luebbers, Loerrach (DE); Patrizio Mattei, Riehen (CH); Cyrille Maugeais, Mulhouse (FR); Werner Mueller, Aesch (CH); Philippe Pflieger, Schwoben (FR)

(73) Assignee: Hoffman-La Roche Inc., Nutley, NJ (US)

( * ) Notice: Subject to any disclaimer, the term of this patent is extended or adjusted under 35 U.S.C. 154(b) by 623 days.

(21) Appl. No.: 11/698,221

(22) Filed: Jan. 25, 2007

(65) Prior Publication Data

US 2007/0185058 A1 Aug. 9, 2007

(30) Foreign Application Priority Data

Feb. 7, 2006 (EP) .................. 06101370

(51) Int. Cl.
*A61K 31/415* (2006.01)
*C07D 231/10* (2006.01)

(52) U.S. Cl. .................. 514/406; 548/356.1; 548/373.1; 548/375.1; 514/403

(58) Field of Classification Search .............. 548/356.1, 548/373.1, 375.1; 514/403, 406
See application file for complete search history.

(56) References Cited

U.S. PATENT DOCUMENTS

| | | | |
|---|---|---|---|
| 7,291,621 B2 * | 11/2007 | Gao et al. | 514/255.03 |
| 7,300,917 B2 * | 11/2007 | Nakade et al. | 514/2 |
| 7,572,823 B2 * | 8/2009 | Conte et al. | 514/406 |

2006/0148830 A1 7/2006 Terakado et al.

FOREIGN PATENT DOCUMENTS

| WO | WO 2004/031118 | 4/2004 |
|---|---|---|
| WO | WO 2005/102388 | 3/2005 |
| WO | WO 2005/100298 A1 | 10/2005 |
| WO | WO 2006/013048 A1 | 2/2006 |

OTHER PUBLICATIONS

Applequist et al., J. Org. Chem., 41, pp. 2262-2266 (1976).
Kelley et al., J. Chem. Res. Miniprint, 12, pp. 2701-2733 (1997).
Le Goff et al., Pharmacology & Therapeutics, 101, pp. 17-38 (2004).
Okamoto et al., Nature, 406, pp. 203-207 (2000).
Liu et al., J. Med. Chem., 46, pp. 4232-4235 (2003).
Austin et al., J. Org. Chem., 46, pp. 2280-2286 (1981).
Bruckner, D., et al., Bioorganic & Medicinal Chemistry Letters, vol. 15, No. 15, pp. 3611-3614 (2005), XP004969906.

* cited by examiner

*Primary Examiner*—Golam M Shameem
(74) *Attorney, Agent, or Firm*—George W. Johnston; Dennis P. Tramaloni; Brian C. Remy

(57) ABSTRACT

Compounds of formula I

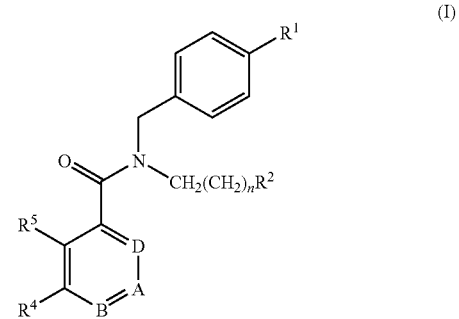

wherein $R^1$, $R^2$, $R^4$, $R^5$, A, B, D and n are as defined, and pharmaceutically acceptable salts thereof, processes for their preparation, their use as pharmaceuticals and pharmaceutical compositions comprising them.

17 Claims, No Drawings

HETEROARYL AND BENZYL AMIDE COMPOUNDS

PRIORITY TO RELATED APPLICATIONS

This application claims the benefit of European Application No. 06101370.2, filed Feb. 7, 2006, which is hereby incorporated by reference in its entirety.

The present invention relates to novel benzamide and heteroarene carboxamide derivatives, processes for their preparation, their use as pharmaceuticals and to pharmaceutical compositions comprising them.

More particularly, the present invention provides in a first aspect a compound of formula I

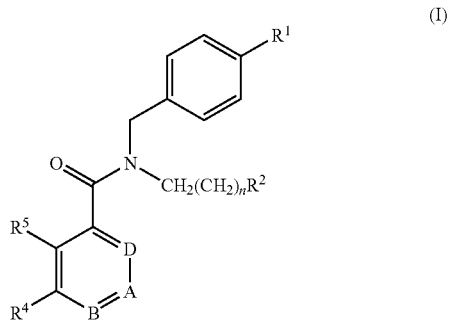

wherein
$R^1$ is $C_1$-$C_6$alkyl, halo-$C_1$-$C_6$alkyl, halo-$C_1$-$C_6$alkoxy, $C_3$-$C_8$cycloalkyl, halo-$C_3$-$C_8$cycloalkyl or tri-$C_1$-$C_6$alkylsilyl;
$R^2$ is hydrogen or a group

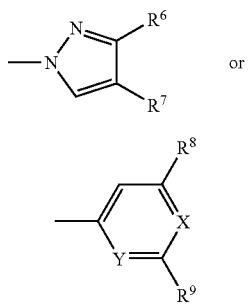

wherein
$R^6$ and $R^7$ are independently hydrogen, $C_1$-$C_6$alkyl, halo-$C_1$-$C_6$alkyl, halogen, $C_3$-$C_8$cycloalkyl, OH or halo-$C_1$-$C_6$alkoxy;
$R^8$ and $R^9$ are independently hydrogen, $C_1$-$C_6$alkyl, halo-$C_1$-$C_6$alkyl, halogen, $C_3$-$C_8$cycloalkyl, OH or halo-$C_1$-$C_6$alkoxy;
X is $CR^{12}$ or N;
Y is CH or N;
wherein X and Y are not N at the same time;
$R^{12}$ is hydrogen, $C_1$-$C_6$alkyl, halo-$C_1$-$C_6$alkyl, halogen, $C_3$-$C_8$cycloalkyl, OH or halo-$C_1$-$C_6$alkoxy;
$R^5$ is hydrogen, $C_1$-$C_6$alkyl, halo-$C_1$-$C_6$alkyl, halogen, $C_3$-$C_8$cycloalkyl, OH or halo-$C_1$-$C_6$alkoxy;
$R^4$ is hydrogen, or is $C_1$-$C_6$alkyl, halo-$C_1$-$C_6$alkyl, halogen, $C_3$-$C_8$cycloalkyl, OH or halo-$C_1$-$C_6$alkoxy when at least one of $R^3$, $R^5$, $R^{10}$ and $R^{11}$ is not hydrogen;
A is $CR^{10}$ or N;
B is $CR^{11}$ or N;
D is $CR^3$ or N;
wherein -B=A- and -A=D- are not —N=N—;
$R^3$ is hydrogen, $C_1$-$C_6$alkyl, halo-$C_1$-$C_6$alkyl, halogen, $C_3$-$C_8$cycloalkyl, OH or halo-$C_1$-$C_6$alkoxy;
$R^{10}$ is hydrogen, or is $C_1$-$C_6$alkyl, halo-$C_1$-$C_6$alkyl, halogen, $C_3$-$C_8$cycloalkyl, OH or halo-$C_1$-$C_6$alkoxy, when at least one of $R^3$, $R^4$, $R^5$ and $R^{11}$ is not hydrogen;
$R^{11}$ is hydrogen or is $C_1$-$C_6$alkyl, halo-$C_1$-$C_6$alkyl, halogen, $C_3$-$C_8$cycloalkyl, OH or halo-$C_1$-$C_6$alkoxy, when at least two of $R^3$, $R^4$, $R^5$ and $R^{10}$ are not hydrogen;
wherein at least two of $R^3$, $R^4$, $R^5$, $R^{10}$ and $R^{11}$ are not hydrogen;
and
n is 1, 2 or 3;
and pharmaceutically acceptable salts thereof.

Examples of $C_1$-$C_6$alkyl include branched and straight-chain monovalent saturated aliphatic hydrocarbon radicals of one to six carbon atoms, e.g. methyl, ethyl, propyl, isopropyl, butyl, isobutyl, tert.-butyl, the isomeric pentyls and the isomeric hexyls.

Examples of halogen include fluorine, chlorine, bromine and iodine.

Examples of halo-$C_1$-$C_6$alkyl include $C_1$-$C_6$alkyl groups as defined above wherein at least one of the hydrogen atoms of the $C_1$-$C_6$alkyl group is replaced by a halogen atom, e.g. fluoro or chloro, e.g. trifluoromethyl, difluoromethyl, fluoromethyl, 1,2,2,2-tetrafluoro-1-trifluoromethyl-ethyl, pentafluoroethyl and chlorodifluoromethyl.

Examples of halo-$C_1$-$C_6$alkoxy include alkoxy groups of formula O-$C_1$-$C_6$alkyl wherein at least one of the hydrogen atoms of the alkoxy group is replaced by a halogen atom, e.g. fluoro or chloro, e.g. trifluoromethoxy, difluoromethoxy, fluoromethoxy and chlorodifluoromethoxy.

Examples of $C_3$-$C_8$cycloalkyl include saturated carbocyclic groups containing from 3 to 8 carbon atoms, such as cyclopropyl, cyclobutyl, cyclopentyl, cyclohexyl, cycloheptyl and cyclooctyl.

Examples of halo-$C_3$-$C_8$cycloalkyl include 1-fluorocyclobutyl.

Examples of tri-$C_1$-$C_6$alkylsilyl include trimethylsilyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

In one embodiment the present invention provides a compound of formula I wherein $R^1$ is $C_1$-$C_6$alkyl, halo-$C_1$-$C_6$alkyl, $C_3$-$C_8$cycloalkyl, $C_3$-$C_8$cycloalkyl or tri-$C_1$-$C_6$alkylsilyl. In another embodiment the present invention provides a compound of formula I wherein $R^1$ is $C_1$-$C_6$alkyl. In still another embodiment the present invention provides a compound of formula I wherein $R^1$ is butyl. In still another embodiment the present invention provides a compound of formula I wherein $R^1$ is tert-butyl.

In one embodiment the present invention provides a compound of formula I wherein $R^2$ is hydrogen.

In another embodiment the present invention provides a compound of formula I wherein $R^2$ is a group (a). In another embodiment the present invention provides a compound of formula I wherein $R^2$ is a group (a) wherein $R^6$ and $R^7$ are independently halo-$C_1$-$C_6$alkyl or halogen. In still another embodiment the present invention provides a compound of formula I wherein $R^2$ is a group (a) wherein $R^6$ halo-$C_1$-$C_6$alkyl and $R^7$ is halogen. In still another embodiment the present invention provides a compound of formula I wherein $R^2$ is a group (a) wherein $R^6$ is $CF_3$ and $R^7$ is Cl.

In another embodiment the present invention provides a compound of formula I wherein $R^2$ is a group (b). In another embodiment the present invention provides a compound of formula I wherein $R^2$ is a group (b) wherein $R^8$ and $R^9$ are independently hydrogen, halo-$C_1$-$C_6$alkyl, halogen, $C_3$-$C_8$cycloalkyl or halo-$C_1$-$C_6$alkoxy. In still another embodiment the present invention provides a compound of formula I wherein $R^2$ is a group (b) wherein $R^8$ and $R^9$ are independently hydrogen, $CF_3$, Cl, F, cyclopropyl or $OCF_3$. In still another embodiment the present invention provides a compound of formula I wherein $R^2$ is a group (b) wherein $R^8$ is hydrogen, $CF_3$, Cl, F, cyclopropyl or $OCF_3$. In another embodiment the present invention provides a compound of formula I wherein $R^2$ is a group (b) wherein $R^8$ and $R^9$ are independently hydrogen, $C_1$-$C_6$alkyl, halo-$C_1$-$C_6$alkyl, halogen, $C_3$-$C_8$cycloalkyl or halo-$C_1$-$C_6$alkoxy. In still another embodiment the present invention provides a compound of formula I wherein $R^2$ is a group (b) wherein $R^8$ and $R^9$ are independently hydrogen, $CH_2CH_3$, $(CH_2)_2CH_3$, $CH(CH_3)_2$, $CF_3$, Br, Cl, F, cyclopropyl or $OCF_3$. In still another embodiment the present invention provides a compound of formula I wherein $R^2$ is a group (b) wherein $R^8$ is hydrogen, $CH_2CH_3$, $(CH_2)_2CH_3$, $CH(CH_3)_2$, $CF_3$, Br, Cl, F, cyclopropyl or $OCF_3$. In still another embodiment the present invention provides a compound of formula I wherein $R^2$ is a group (b) wherein $R^9$ is hydrogen, Cl or F. In still another embodiment the present invention provides a compound of formula I wherein $R^2$ is a group (b) wherein $R^9$ is hydrogen or F.

In another embodiment the present invention provides a compound of formula I wherein $R^2$ is a group (b) wherein X is $CR^{12}$. In still another embodiment the present invention provides a compound of formula I wherein $R^2$ is a group (b) wherein X is $CR^{12}$ wherein $R^{12}$ is hydrogen, $C_1$-$C_6$alkyl, halo-$C_1$-$C_6$alkyl, halogen or halo-$C_1$-$C_6$alkoxy. In still another embodiment the present invention provides a compound of formula I wherein $R^2$ is a group (b) wherein X is $CR^{12}$ wherein $R^{12}$ is hydrogen, $C_1$-$C_6$alkyl, halo-$C_1$-$C_6$alkyl or halogen. In still another embodiment the present invention provides a compound of formula I wherein $R^2$ is a group (b) wherein X is $CR^{12}$ wherein $R^{12}$ is hydrogen or halogen. In still another embodiment the present invention provides a compound of formula I wherein $R^2$ is a group (b) wherein X is $CR^{12}$ wherein $R^{12}$ is hydrogen, Cl or F. In still another embodiment the present invention provides a compound of formula I wherein $R^2$ is a group (b) wherein X is $CR^{12}$ wherein $R^{12}$ is hydrogen, $C_1$-$C_6$alkyl, halo-$C_1$-$C_6$alkyl, halogen, $C_3$-$C_8$cycloalkyl or halo-$C_1$-$C_6$alkoxy. In still another embodiment the present invention provides a compound of formula I wherein $R^2$ is a group (b) wherein X is $CR^{12}$ wherein $R^{12}$ is hydrogen, $C_1$-$C_6$alkyl, halo-$C_1$-$C_6$alkyl, halogen or $C_3$-$C_8$cycloalkyl. In still another embodiment the present invention provides a compound of formula I wherein $R^2$ is a group (b) wherein X is $CR^{12}$ wherein $R^{12}$ is hydrogen, halogen or $C_3$-$C_8$cycloalkyl. In still another embodiment the present invention provides a compound of formula I wherein $R^2$ is a group (b) wherein X is $CR^{12}$ wherein $R^{12}$ is hydrogen, Cl, F or cyclopropyl.

In another embodiment the present invention provides a compound of formula I wherein $R^2$ is a group (b) wherein X is or N and Y is CH.

In another embodiment the present invention provides a compound of formula I wherein $R^2$ is a group (b) wherein Y is CH.

In another embodiment the present invention provides a compound of formula I wherein $R^2$ is a group (b) wherein Y is N and X is $CR^{12}$.

In another embodiment the present invention provides a compound of formula I wherein A is $CR^{10}$. In still another embodiment the present invention provides a compound of formula I wherein A is $CR^{10}$ wherein $R^{10}$ is hydrogen, or is halo-$C_1$-$C_6$alkyl, halogen, $C_3$-$C_8$cycloalkyl or OH, when at least one of $R^3$, $R^4$, $R^5$ and $R^{11}$ is not hydrogen. In still another embodiment the present invention provides a compound of formula I wherein A is $CR^{10}$ wherein $R^{10}$ is halo-$C_1$-$C_6$alkyl or halogen, when at least one of $R^3$, $R^4$, $R^5$ and $R^{11}$ is not hydrogen. In still another embodiment the present invention provides a compound of formula I wherein A is $CR^{10}$ wherein $R^{10}$ is $CF_3$ or Cl, when at least one of $R^3$, $R^4$, $R^5$ and $R^{11}$ is not hydrogen.

In another embodiment the present invention provides a compound of formula I wherein A is N and B and D are not N.

In another embodiment the present invention provides a compound of formula I wherein B is $CR^{11}$. In another embodiment the present invention provides a compound of formula I wherein B is $CR^{11}$ wherein $R^{11}$ is hydrogen or is halogen, when at least two of $R^3$, $R^4$, $R^5$ and $R^{10}$ are not hydrogen. In another embodiment the present invention provides a compound of formula I wherein B is $CR^{11}$ wherein $R^{11}$ is hydrogen or is F or Cl, when at least two of $R^3$, $R^4$, $R^5$ and $R^{10}$ are not hydrogen. In still another embodiment the present invention provides a compound of formula I wherein B is $CR^{11}$ wherein $R^{11}$ is hydrogen.

In another embodiment the present invention provides a compound of formula I wherein B is N and A is not N.

In another embodiment the present invention provides a compound of formula I wherein D is $CR^3$. In still another embodiment the present invention provides a compound of formula I wherein D is $CR^3$ wherein $R^3$ is hydrogen.

In another embodiment the present invention provides a compound of formula I wherein D is N.

In another embodiment the present invention provides a compound of formula I wherein $R^5$ is hydrogen, halo-$C_1$-$C_6$alkyl, halogen or OH. In still another embodiment the present invention provides a compound of formula I wherein $R^5$ is hydrogen, halo-$C_1$-$C_6$alkyl or halogen. In still another embodiment the present invention provides a compound of formula I wherein $R^5$ is hydrogen or halogen. In still another embodiment the present invention provides a compound of formula I wherein $R^5$ is hydrogen or F.

In another embodiment the present invention provides a compound of formula I wherein $R^4$ is hydrogen, or is $C_1$-$C_6$alkyl, halo-$C_1$-$C_6$alkyl or halogen when at least one of $R^3$, $R^5$, $R^{10}$ and $R^{11}$ is not hydrogen. In still another embodiment the present invention provides a compound of formula I wherein $R^4$ is halo-$C_1$-$C_6$alkyl or halogen and at least one of $R^3$, $R^5$, $R^{10}$ and $R^{11}$ is not hydrogen. In still another embodiment the present invention provides a compound of formula I wherein $R^4$ is $CF_3$ or Cl and at least one of $R^3$, $R^5$, $R^{10}$ and $R^{11}$ is not hydrogen. In still another embodiment the present invention provides a compound of formula I wherein $R^4$ is $C_1$-$C_6$alkyl, halo-$C_1$-$C_6$alkyl or halogen and at least one of $R^3$, $R^5$, $R^{10}$ and $R^{11}$ is not hydrogen. In still another embodiment the present invention provides a compound of formula I wherein $R^4$ is $CH_2CH_3$, $CF_3$ or Cl and at least one of $R^3$, $R^5$, $R^{10}$ and $R^{11}$ is not hydrogen.

The present invention provides compounds of formula I wherein at least two of $R^3$, $R^4$, $R^5$, $R^{10}$ and $R^{11}$ are not hydrogen.

In another embodiment the present invention provides a compound of formula I wherein n is 1.

In one embodiment the present invention provides a compound of formula I wherein
$R^1$ is $C_1$-$C_6$alkyl, halo-$C_1$-$C_6$alkyl, halo-$C_1$-$C_6$alkoxy, $C_3$-$C_8$cycloalkyl, halo-$C_3$-$C_8$cycloalkyl or tri-$C_1$-$C_6$alkylsilyl;
$R^2$ is hydrogen;
$R^5$ is hydrogen, $C_1$-$C_6$alkyl, halo-$C_1$-$C_6$alkyl, halogen, $C_3$-$C_8$cycloalkyl, OH or halo-$C_1$-$C_6$alkoxy;
$R^4$ is hydrogen, or is $C_1$-$C_6$alkyl, halo-$C_1$-$C_6$alkyl, halogen, $C_3$-$C_8$cycloalkyl, OH or halo-$C_1$-$C_6$alkoxy when at least one of $R^3$, $R^5$, $R^{10}$ and $R^{11}$ is not hydrogen;
A is $CR^{10}$ or N;
B is $CR^{11}$ or N;
D is $CR^3$ or N;
wherein -B=A- and -A=D- are not —N=N—;
$R^3$ is hydrogen, $C_1$-$C_6$alkyl, halo-$C_1$-$C_6$alkyl, halogen, $C_3$-$C_8$cycloalkyl, OH or halo-$C_1$-$C_6$alkoxy;
$R^{10}$ is hydrogen, or is $C_1$-$C_6$alkyl, halo-$C_1$-$C_6$alkyl, halogen, $C_3$-$C_8$cycloalkyl, OH or halo-$C_1$-$C_6$alkoxy, when at least one of $R^3$, $R^4$, $R^5$ and $R^{11}$ is not hydrogen;
$R^{11}$ is hydrogen or is $C_1$-$C_6$alkyl, halo-$C_1$-$C_6$alkyl, halogen, $C_3$-$C_8$cycloalkyl, OH or halo-$C_1$-$C_6$alkoxy, when at least two of $R^3$, $R^4$, $R^5$ and $R^{10}$ are not hydrogen;
wherein at least two of $R^3$, $R^4$, $R^5$, $R^{10}$ and $R^{11}$ are not hydrogen;
and
n is 1, 2 or 3;
and pharmaceutically acceptable salts thereof.

In one embodiment the present invention provides a compound of formula I wherein
$R^1$ is $C_1$-$C_6$alkyl, halo-$C_1$-$C_6$alkyl, halo-$C_1$-$C_6$alkoxy, $C_3$-$C_8$cycloalkyl, halo-$C_3$-$C_8$cycloalkyl or tri-$C_1$-$C_6$alkylsilyl;
$R^2$ is a group

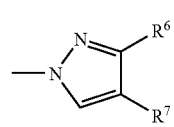

(a)

wherein $R^6$ and $R^7$ are independently hydrogen, $C_1$-$C_6$alkyl, halo-$C_1$-$C_6$alkyl, halogen, $C_3$-$C_8$cycloalkyl, OH or halo-$C_1$-$C_6$alkoxy;
$R^5$ is hydrogen, $C_1$-$C_6$alkyl, halo-$C_1$-$C_6$alkyl, halogen, $C_3$-$C_8$cycloalkyl, OH or halo-$C_1$-$C_6$alkoxy;
$R^4$ is hydrogen, or is $C_1$-$C_6$alkyl, halo-$C_1$-$C_6$alkyl, halogen, $C_3$-$C_8$cycloalkyl, OH or halo-$C_1$-$C_6$alkoxy when at least one of $R^3$, $R^5$, $R^{10}$ and $R^{11}$ is not hydrogen;
A is $CR^{10}$ or N;
B is $CR^{11}$ or N;
D is $CR^3$ or N;
wherein -B=A- and -A=D- are not —N=N—;
$R^3$ is hydrogen, $C_1$-$C_6$alkyl, halo-$C_1$-$C_6$alkyl, halogen, $C_3$-$C_8$cycloalkyl, OH or halo-$C_1$-$C_6$alkoxy;
$R^{10}$ is hydrogen, or is $C_1$-$C_6$alkyl, halo-$C_1$-$C_6$alkyl, halogen, $C_3$-$C_8$cycloalkyl, OH or halo-$C_1$-$C_6$alkoxy, when at least one of $R^3$, $R^4$, $R^5$ and $R^{11}$ is not hydrogen;
$R^{11}$ is hydrogen or is $C_1$-$C_6$alkyl, halo-$C_1$-$C_6$alkyl, halogen, $C_3$-$C_8$cycloalkyl, OH or halo-$C_1$-$C_6$alkoxy, when at least two of $R^3$, $R^4$, $R^5$ and $R^{10}$ are not hydrogen;
wherein at least two of $R^3$, $R^4$, $R^5$, $R^{10}$ and $R^{11}$ are not hydrogen;
and
n is 1, 2 or 3;
and pharmaceutically acceptable salts thereof.

In one embodiment the present invention provides a compound of formula I wherein
$R^1$ is $C_1$-$C_6$alkyl, halo-$C_1$-$C_6$alkyl, halo-$C_1$-$C_6$alkoxy, $C_3$-$C_8$cycloalkyl, halo-$C_3$-$C_8$cycloalkyl or tri-$C_1$-$C_6$alkylsilyl;
$R^2$ is a group

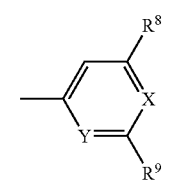

(b)

wherein
$R^8$ and $R^9$ are independently hydrogen, $C_1$-$C_6$alkyl, halo-$C_1$-$C_6$alkyl, halogen, $C_3$-$C_8$cycloalkyl, OH or halo-$C_1$-$C_6$alkoxy;
X is $CR^{12}$ or N;
Y is CH or N;
wherein X and Y are not N at the same time;
$R^{12}$ is hydrogen, $C_1$-$C_6$alkyl, halo-$C_1$-$C_6$alkyl, halogen, $C_3$-$C_8$cycloalkyl, OH or halo-$C_1$-$C_6$alkoxy;

$R^5$ is hydrogen, $C_1$-$C_6$alkyl, halo-$C_1$-$C_6$alkyl, halogen, $C_3$-$C_8$cycloalkyl, OH or halo-$C_1$-$C_6$alkoxy;

$R^4$ is hydrogen, or is $C_1$-$C_6$alkyl, halo-$C_1$-$C_6$alkyl, halogen, $C_3$-$C_8$cycloalkyl, OH or halo-$C_1$-$C_6$alkoxy when at least one of $R^3$, $R^5$, $R^{10}$ and $R^{11}$ is not hydrogen;

A is $CR^{10}$ or N;

B is $CR^{11}$ or N;

D is $CR^3$ or N;

wherein -B=A- and -A=D- are not —N=N—;

$R^3$ is hydrogen, $C_1$-$C_6$alkyl, halo-$C_1$-$C_6$alkyl, halogen, $C_3$-$C_8$cycloalkyl, OH or halo-$C_1$-$C_6$alkoxy;

$R^{10}$ is hydrogen, or is $C_1$-$C_6$alkyl, halo-$C_1$-$C_6$alkyl, halogen, $C_3$-$C_8$cycloalkyl, OH or halo-$C_1$-$C_6$alkoxy, when at least one of $R^3$, $R^4$, $R^5$ and $R^{11}$ is not hydrogen;

$R^{11}$ is hydrogen or is $C_1$-$C_6$alkyl, halo-$C_1$-$C_6$alkyl, halogen, $C_3$-$C_8$cycloalkyl, OH or halo-$C_1$-$C_6$alkoxy, when at least two of $R^3$, $R^4$, $R^5$ and $R^{10}$ are not hydrogen;

wherein at least two of $R^3$, $R^4$, $R^5$, $R^{10}$ and $R^{11}$ are not hydrogen;

and n is 1, 2 or 3;

and pharmaceutically acceptable salts thereof.

In one embodiment the present invention provides a compound of formula I wherein $R^1$ is $C_1$-$C_6$alkyl, halo-$C_1$-$C_6$alkyl, halo-$C_1$-$C_6$alkoxy, $C_3$-$C_8$cycloalkyl, halo-$C_3$-$C_8$cycloalkyl or tri-$C_1$-$C_6$alkylsilyl;

$R^2$ is hydrogen or a group

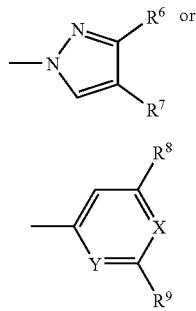

wherein $R^6$ and $R^7$ are independently hydrogen, $C_1$-$C_6$alkyl, halo-$C_1$-$C_6$alkyl, halogen, $C_3$-$C_8$cycloalkyl, OH or halo-$C_1$-$C_6$alkoxy;

$R^8$ and $R^9$ are independently hydrogen, $C_1$-$C_6$alkyl, halo-$C_1$-$C_6$alkyl, halogen, $C_3$-$C_8$cycloalkyl, OH or halo-$C_1$-$C_6$alkoxy;

X is $CR^{12}$ or N;

Y is CH or N;

wherein X and Y are not N at the same time;

$R^{12}$ is hydrogen, $C_1$-$C_6$alkyl, halo-$C_1$-$C_6$alkyl, halogen, $C_3$-$C_8$cycloalkyl, OH or halo-$C_1$-$C_6$alkoxy;

$R^5$ is hydrogen, $C_1$-$C_6$alkyl, halo-$C_1$-$C_6$alkyl, halogen, $C_3$-$C_8$cycloalkyl, OH or halo-$C_1$-$C_6$alkoxy;

$R^4$ is hydrogen, or is $C_1$-$C_6$alkyl, halo-$C_1$-$C_6$alkyl, halogen, $C_3$-$C_8$cycloalkyl, OH or halo-$C_1$-$C_6$alkoxy when at least one of $R^3$, $R^5$, $R^{10}$ and $R^{11}$ is not hydrogen;

A is $CR^{10}$;

B is $CR^{11}$ or N;

D is $CR^3$ or N;

$R^3$ is hydrogen, $C_1$-$C_6$alkyl, halo-$C_1$-$C_6$alkyl, halogen, $C_3$-$C_8$cycloalkyl, OH or halo-$C_1$-$C_6$alkoxy;

$R^{10}$ is hydrogen, or is $C_1$-$C_6$alkyl, halo-$C_1$-$C_6$alkyl, halogen, $C_3$-$C_8$cycloalkyl, OH or halo-$C_1$-$C_6$alkoxy, when at least one of $R^3$, $R^4$, $R^5$ and $R^{11}$ is not hydrogen;

$R^{11}$ is hydrogen or is $C_1$-$C_6$alkyl, halo-$C_1$-$C_6$alkyl, halogen, $C_3$-$C_8$cycloalkyl, OH or halo-$C_1$-$C_6$alkoxy, when at least two of $R^3$, $R^4$, $R^5$ and $R^{10}$ are not hydrogen;

wherein at least two of $R^3$, $R^4$, $R^5$, $R^{10}$ and $R^{11}$ are not hydrogen;

and n is 1, 2 or 3;

and pharmaceutically acceptable salts thereof.

In one embodiment the present invention provides a compound of formula I wherein $R^1$ is $C_1$-$C_6$alkyl, halo-$C_1$-$C_6$alkyl, halo-$C_1$-$C_6$alkoxy, $C_3$-$C_8$cycloalkyl, halo-$C_3$-$C_8$cycloalkyl or tri-$C_1$-$C_6$alkylsilyl;

$R^2$ is hydrogen or a group

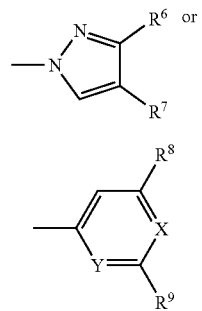

wherein $R^6$ and $R^7$ are independently hydrogen, $C_1$-$C_6$alkyl, halo-$C_1$-$C_6$alkyl, halogen, $C_3$-$C_8$cycloalkyl, OH or halo-$C_1$-$C_6$alkoxy;

$R^8$ and $R^9$ are independently hydrogen, $C_1$-$C_6$alkyl, halo-$C_1$-$C_6$alkyl, halogen, $C_3$-$C_8$cycloalkyl, OH or halo-$C_1$-$C_6$alkoxy;

X is $CR^{12}$ or N;

Y is CH or N;

wherein X and Y are not N at the same time;

$R^{12}$ is hydrogen, $C_1$-$C_6$alkyl, halo-$C_1$-$C_6$alkyl, halogen, $C_3$-$C_8$cycloalkyl, OH or halo-$C_1$-$C_6$alkoxy;

$R^5$ is hydrogen, $C_1$-$C_6$alkyl, halo-$C_1$-$C_6$alkyl, halogen, $C_3$-$C_8$cycloalkyl, OH or halo-$C_1$-$C_6$alkoxy;

$R^4$ is hydrogen, or is $C_1$-$C_6$alkyl, halo-$C_1$-$C_6$alkyl, halogen, $C_3$-$C_8$cycloalkyl, OH or halo-$C_1$-$C_6$alkoxy when at least one of $R^3$, $R^5$ and $R^{11}$ is not hydrogen;

A is N;

B is $CR^{11}$;

D is $CR^3$;

$R^3$ is hydrogen, $C_1$-$C_6$alkyl, halo-$C_1$-$C_6$alkyl, halogen, $C_3$-$C_8$cycloalkyl, OH or halo-$C_1$-$C_6$alkoxy;

$R^{11}$ is hydrogen or is $C_1$-$C_6$alkyl, halo-$C_1$-$C_6$alkyl, halogen, $C_3$-$C_8$cycloalkyl, OH or halo-$C_1$-$C_6$alkoxy, when at least two of $R^3$, $R^4$, $R^5$ and $R^{10}$ are not hydrogen;

wherein at least two of $R^3$, $R^4$, $R^5$, $R^{10}$ and $R^{11}$ are not hydrogen;

and n is 1, 2 or 3;

and pharmaceutically acceptable salts thereof.

In one embodiment the present invention provides a compound of formula I wherein $R^1$ is $C_1$-$C_6$alkyl, halo-$C_1$-$C_6$alkyl, halo-$C_1$-$C_6$alkoxy, $C_3$-$C_8$cycloalkyl, halo-$C_3$-$C_8$cycloalkyl or tri-$C_1$-$C_6$alkylsilyl;

$R^2$ is hydrogen or a group

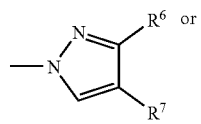
(a)

or

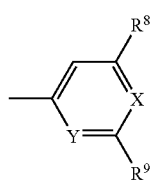
(b)

wherein $R^6$ and $R^7$ are independently hydrogen, $C_1$-$C_6$alkyl, halo-$C_1$-$C_6$alkyl, halogen, $C_3$-$C_8$cycloalkyl, OH or halo-$C_1$-$C_6$alkoxy;

$R^8$ and $R^9$ are independently hydrogen, $C_1$-$C_6$alkyl, halo-$C_1$-$C_6$alkyl, halogen, $C_3$-$C_8$cycloalkyl, OH or halo-$C_1$-$C_6$alkoxy;

X is $CR^{12}$ or N;

Y is CH or N;

wherein X and Y are not N at the same time;

$R^{12}$ is hydrogen, $C_1$-$C_6$alkyl, halo-$C_1$-$C_6$alkyl, halogen, $C_3$-$C_8$cycloalkyl, OH or halo-$C_1$-$C_6$alkoxy;

$R^5$ is hydrogen, $C_1$-$C_6$alkyl, halo-$C_1$-$C_6$alkyl, halogen, $C_3$-$C_8$cycloalkyl, OH or halo-$C_1$-$C_6$alkoxy;

$R^4$ is hydrogen, or is $C_1$-$C_6$alkyl, halo-$C_1$-$C_6$alkyl, halogen, $C_3$-$C_8$cycloalkyl, OH or halo-$C_1$-$C_6$alkoxy when at least one of $R^3$, $R^5$, $R^{10}$ and $R^{11}$ is not hydrogen;

A is $CR^{10}$;

B is $CR^{11}$ or N;

D is $CR^3$;

$R^3$ is hydrogen, $C_1$-$C_6$alkyl, halo-$C_1$-$C_6$alkyl, halogen, $C_3$-$C_8$cycloalkyl, OH or halo-$C_1$-$C_6$alkoxy;

$R^{10}$ is hydrogen, or is $C_1$-$C_6$alkyl, halo-$C_1$-$C_6$alkyl, halogen, $C_3$-$C_8$cycloalkyl, OH or halo-$C_1$-$C_6$alkoxy, when at least one of $R^3$, $R^4$, $R^5$ and $R^{11}$ is not hydrogen;

$R^{11}$ is hydrogen or is $C_1$-$C_6$alkyl, halo-$C_1$-$C_6$alkyl, halogen, $C_3$-$C_8$cycloalkyl, OH or halo-$C_1$-$C_6$alkoxy, when at least two of $R^3$, $R^4$, $R^5$ and $R^{10}$ are not hydrogen;

wherein at least two of $R^3$, $R^4$, $R^5$, $R^{10}$ and $R^{11}$ are not hydrogen;

and n is 1, 2 or 3;

and pharmaceutically acceptable salts thereof.

In one embodiment the present invention provides a compound of formula I wherein $R^1$ is $C_1$-$C_6$alkyl;

$R^2$ is a group

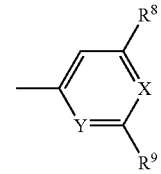
(b)

wherein $R^8$ and $R^9$ are independently hydrogen, halo-$C_1$-$C_6$alkyl, halogen, $C_3$-$C_8$cycloalkyl or halo-$C_1$-$C_6$alkoxy;

X is $CR^{12}$;

Y is CH;

$R^{12}$ is hydrogen or halogen;

$R^5$ is hydrogen or halogen;

$R^4$ is halo-$C_1$-$C_6$alkyl or halogen;

A is $CR^{10}$;

B is $CR^{11}$ or N;

D is $CR^3$;

$R^3$ is hydrogen;

$R^{10}$ is halo-$C_1$-$C_6$alkyl or halogen;

$R^{11}$ is hydrogen;

and n is 1, 2 or 3;

and pharmaceutically acceptable salts thereof.

In one embodiment the present invention provides a compound of formula I wherein $R^1$ is $C_1$-$C_6$alkyl;

$R^2$ is a group

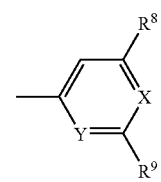
(b)

wherein $R^8$ and $R^9$ are independently hydrogen, halo-$C_1$-$C_6$alkyl, halogen, $C_3$-$C_8$cycloalkyl or halo-$C_1$-$C_6$alkoxy;

X is $CR^{12}$;

Y is CH;

$R^{12}$ is hydrogen, halogen or $C_3$-$C_8$cycloalkyl;

$R^5$ is hydrogen or halogen;

$R^4$ is $C_1$-$C_6$alkyl, halo-$C_1$-$C_6$alkyl or halogen;

A is $CR^{10}$;

B is $CR^{11}$ or N;

D is $CR^3$;

$R^3$ is hydrogen;

$R^{10}$ is halo-$C_1$-$C_6$alkyl or halogen;

$R^{11}$ is hydrogen;

and n is 1, 2 or 3;

and pharmaceutically acceptable salts thereof.

In addition to the foregoing the present invention also provides a process for the production of a compound of formula I

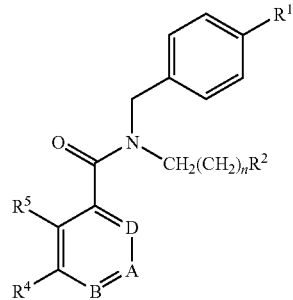
(I)

wherein
$R^1$ is $C_1$-$C_6$alkyl, halo-$C_1$-$C_6$alkyl, halo-$C_1$-$C_6$alkoxy, $C_3$-$C_8$cycloalkyl, halo-$C_3$-$C_8$cycloalkyl or tri-$C_1$-$C_6$alkylsilyl;
$R^2$ is hydrogen or a group

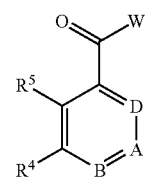
(a)

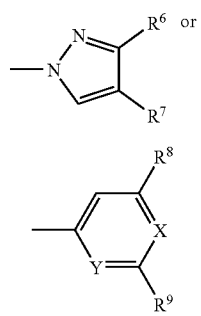
(b)

wherein
$R^6$ and $R^7$ are independently hydrogen, $C_1$-$C_6$alkyl, halo-$C_1$-$C_6$alkyl, halogen, $C_3$-$C_8$cycloalkyl, OH or halo-$C_1$-$C_6$alkoxy;
$R^8$ and $R^9$ are independently hydrogen, $C_1$-$C_6$alkyl, halo-$C_1$-$C_6$alkyl, halogen, $C_3$-$C_8$cycloalkyl, OH or halo-$C_1$-$C_6$alkoxy;
X is $CR^{12}$ or N;
Y is CH or N;
wherein X and Y are not N at the same time;
$R^{12}$ is hydrogen, $C_1$-$C_6$alkyl, halo-$C_1$-$C_6$alkyl, halogen, $C_3$-$C_8$cycloalkyl, OH or halo-$C_1$-$C_6$alkoxy;
$R^3$ and $R^5$ are independently hydrogen, $C_1$-$C_6$alkyl, halo-$C_1$-$C_6$alkyl, halogen, $C_3$-$C_8$cycloalkyl, OH or halo-$C_1$-$C_6$alkoxy;
$R^4$ is hydrogen, or is $C_1$-$C_6$alkyl, halo-$C_1$-$C_6$alkyl, halogen, $C_3$-$C_8$cycloalkyl, OH or halo-$C_1$-$C_6$alkoxy when at least one of $R^3$, $R^5$, $R^{10}$ and $R^{11}$ is not hydrogen;
A is $CR^{10}$ or N;
B is $CR^{11}$ or N;
D is $CR^3$ or N;
wherein -B=A- and -A=D- are not —N=N—;
$R^{10}$ is hydrogen, or is $C_1$-$C_6$alkyl, halo-$C_1$-$C_6$alkyl, halogen, $C_3$-$C_8$cycloalkyl, OH or halo-$C_1$-$C_6$alkoxy, when at least one of $R^3$, $R^4$, $R^5$ and $R^{11}$ is not hydrogen;
$R^{11}$ is hydrogen or is $C_1$-$C_6$alkyl, halo-$C_1$-$C_6$alkyl, halogen, $C_3$-$C_8$cycloalkyl, OH or halo-$C_1$-$C_6$alkoxy, when at least two of $R^3$, $R^4$, $R^5$ and $R^{10}$ are not hydrogen;
wherein at least two of $R^3$, $R^4$, $R^5$, $R^{10}$ and $R^{11}$ are not hydrogen;
and
n is 1, 2 or 3;
which process comprises reacting an acid derivative, a compound of formula II

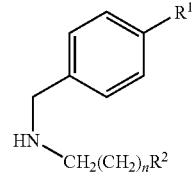
(II)

wherein $R^4$, $R^5$, A, B and D have the above meanings and W is hydroxy, OLi, ONa, OK or halogen, e.g. Cl, with a secondary amine derivative, a compound of formula III (III)

wherein $R^1$, $R^2$ and n have the above meanings.

If carboxylic acids (W=OH) or carboxylate salts (W=OLi, ONa, OK) of formula II are used in this process, standard peptide coupling reagents can be applied to activate the acid prior to the coupling reaction. Typically, the acid derivative II (R=OH, OLi, ONa, OK) is mixed with a coupling reagent such as EDC or EDC.HCl, DCC, HBTU or TBTU in an inert solvent such as N,N-dimethylformamide, dimethylacetamide (DMA) or dichloromethane (DCM) together with the appropriate secondary amine derivative III. Optionally a base (e.g. N,N-diisopropylethyl amine, triethylamine, N-methyl morpholine) and/or 1-hydroxybenzotriazole (HOBT) can be added. The reaction mixture is stirred for 1 to 24 h at a temperature of about −30° C. to about 70° C. (e.g. ambient temperature).

Alternatively, acid chlorides (W=Cl) can be reacted with secondary amine derivatives III to obtain formula (I) compounds, using standard protocols.

Acid derivatives of formula II are commercially available or can be prepared as described in the example section.

Secondary amines of the general formula III can be synthesized by standard methods. They may be synthesized as outlined below.

Compounds of formula III

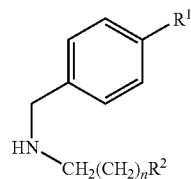
(III)

wherein
R$^1$ is C$_1$-C$_6$alkyl, halo-C$_1$-C$_6$alkyl, halo-C$_1$-C$_6$alkoxy, C$_3$-C$_8$cycloalkyl, halo-C$_3$-C$_8$cycloalkyl or tri-C$_1$-C$_6$alkylsilyl;
R$^2$ is hydrogen or a group

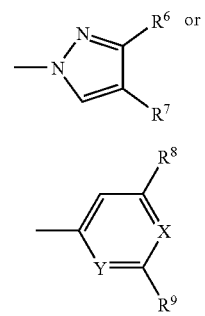

(a)

(b)

wherein
R$^6$ and R$^7$ are independently hydrogen, C$_1$-C$_6$alkyl, halo-C$_1$-C$_6$alkyl, halogen, C$_3$-C$_8$cycloalkyl, OH or halo-C$_1$-C$_6$alkoxy;
R$^8$ and R$^9$ are independently hydrogen, C$_1$-C$_6$alkyl, halo-C$_1$-C$_6$alkyl, halogen, C$_3$-C$_8$cycloalkyl, OH or halo-C$_1$-C$_6$alkoxy;
X is CR$^{12}$ or N;
Y is CH or N;
wherein X and Y are not N at the same time;
R$^{12}$ is hydrogen, C$_1$-C$_6$alkyl, halo-C$_1$-C$_6$alkyl, halogen, C$_3$-C$_8$cycloalkyl, OH or halo-C$_1$-C$_6$alkoxy; and
n is 1, 2 or 3;
may be prepared by reductive amination of a benzaldehyde derivative, a compound of formula IV

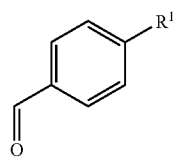
(IV)

wherein R$^1$ is as defined above,
with an amine, a compound of formula V

(V)

wherein R$^2$ and n are as defined above.
The necessary starting amines and aldehydes are commercially available or are synthesized using standard methods as e.g. described in the example section.

Secondary amines III may alternatively be synthesized from amide derivatives, compounds of formula VII

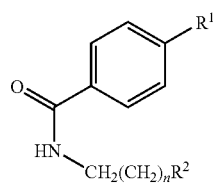
(VII)

wherein R$^1$, R$^2$ and n are as defined above.
Amide derivatives, compounds of formula VII are available by the coupling of benzoic acid derivatives, compounds of formula VI

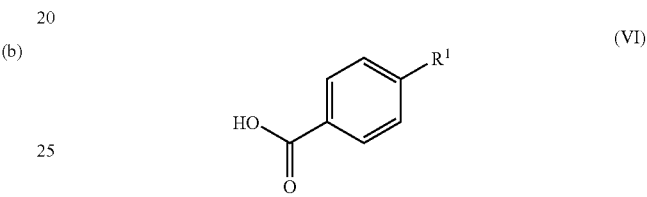
(VI)

wherein R$^1$ is as defined above,
with a compound of formula V.

The necessary starting benzoic acids are commercially available or may be synthesized using standard methods as e.g. described in the example section.

The following abbreviations are used: RT: room temperature; THF: tetrahydrofuran; DMF: N,N-dimethylformamide; DCM: dichloromethane In general, the nomenclature used in this Application is based on AUTONOM™ v.4.0, a Beilstein Institute computerized system for the generation of IUPAC systematic nomenclature.

ALDEHYDES (ACIDS) (COMPOUNDS OF FORMULA IV AND VI)

EXAMPLE S1-A

Preparation of 4-cyclopropyl benzaldehyde

To a solution of 1-bromo-4-cyclopropylbenzene [synthesized in analogy to a procedure described in J. Org. Chem. 1976, 41, 2262-2266] (1.58 g, 8.04 mmol) in THF at −78° C. was added n-BuLi (5.08 ml, 1.6M solution in hexane, 8.11 mmol) and the reaction mixture was stirred at −78° C. for 10 min. DMF (1.25 ml, 16.08 mmol) was then added and the reaction mixture was stirred at −78° C. for 15 min. The reaction mixture was then warmed to 0° C. slowly (over 2 h) and stirred at 0° C. for 1 h. The reaction was quenched with sat. NH$_4$Cl $_{(aq)}$ solution and the aqueous phase was extracted with ether. The organic layer was washed with brine, dried (MgSO$_4$), filtered and concentrated in vacuo to give a residue which was purified by flash column chromatography (1:9 diethyl ether/pentane) to give 4-cyclopropyl benzaldehyde (1.10 g, 94%) as a colorless oil. $^1$H NMR (CDCl$_3$, 300 MHz): δ 9.94 (s, 1H), 7.76 (d, J=8.5 Hz, 2H), 7.19 (d, J=8.5 Hz, 2H), 1.97 (m, 1H), 1.13-1.06 (m, 2H), 0.84-0.78 (m, 2H).

EXAMPLE S2-A

Preparation of 4-cyclobutyl benzaldehyde a) Preparation of 1-(4-bromophenyl)-cyclobutanol To a solution of 1,4-dibromobenzene (1.00 g, 4.24 mmol) at −78° C. in ether (20 ml) was added n-BuLi (2.65 ml, 1.6 M solution in hexane, 4.24 mmol) and the reaction mixture was stirred at −78° C. for 30 min. Cyclobutanone (348 µl, 4.66 mmol) was then added and the reaction mixture was stirred at −78° C. for 15 min. The reaction mixture was then slowly (over 2 h) warmed to 0° C. and stirred for a further 1 h. Water was added followed by sat. $NH_4Cl$ and the reaction mixture was extracted with ether. The organic layer was washed with brine, dried ($MgSO_4$), filtered and concentrated in vacuo to give a residue which was purified by flash column chromatography (1:4 ether/pentane) to give 1-(4-bromophenyl)-cyclobutanol (330 mg, 34%) as a colorless oil. $^1H$ NMR ($CDCl_3$, 300 MHz): δ 7.50 (d, J=8.5 Hz, 2H), 7.38 (d, J=8.5 Hz, 2H), 2.57-2.48 (m, 2H), 2.41-2.31 (m, 2H), 2.02 (m, 1H), 1.69 (m, 1H).

b) Preparation of 1-bromo-4-cyclobutyl-benzene

To a solution of 1.37 g of 1-(4-bromophenyl)-cyclobutanol (6 mmol) in 15 ml DCM were added 1.15 ml of triethylsilane (7.2 mmol) and the mixture was cooled to −78° C. Then 1.15 ml of boron trifluoride diethyl etherate complex were added and the reaction mixture was warmed to −40° C. and stirred for 8 h. The reaction was then quenched by addition of 10% aqueous $KHCO_3$ and the mixture was extracted three times with DCM. The combined extracts were washed with brine, dried with magnesium sulfate and concentrated. The remaining residue was purified by column chromatography (silica gel; cyclohexane) to give 0.84 g (66%) of 1-bromo-4-cyclobutyl-benzene as a colorless liquid. $^{1H}$ NMR ($CDCl_3$, 300 MHz): δ 1.85 (m, 1H), 1.92-2.18 (m, 3H), 2.33 (m, 2H), 3.49 (quint, J=8.5 Hz, 1H), 7.08 (d, J=8.5 Hz, 2H), 7.40 (d, J=8.5 Hz, 2H).

c) Preparation of 4-cyclobutyl-benzaldehyde

The title compound was synthesized in analogy to 4-cyclopropyl benzaldehyde (described in example S1-A) using 830 mg of 1-bromo-4-cyclobutyl-benzene (3.93 mmol), 2.7 ml of a 1.6 molar solution of n-BuLi in hexane (4.32 mmol) and 605 µl of DMF (7.86 mmol). The isolated residue was purified by flash column chromatography (5:95 EtOAc/cyclohexane) to give 422 mg of 4-cyclobutyl-benzaldehyde (67%) as a colorless liquid. $^{1H}$ NMR ($CDCl_3$, 300 MHz): δ 1.89 (m, 1H), 1.97-2.26 (m, 3H), 2.40 (m, 2H), 3.63 (quint, J=8.5 Hz, 1H), 7.36 (d, J=8.0 Hz, 2H), 7.81 (d, J=8.0 Hz, 2H), 9.97 (s, 1H).

EXAMPLE S3-A

Preparation of 4-(1-fluoro-cyclobutyl)-benzaldehyde a) Preparation of 1-bromo-4-(1-fluoro-cyclobutyl)-benzene To a solution of 5.66 g of 1-(4-bromophenyl)-cyclobutanol (24.92 mmol, described in example S2-A) in 70 ml DCM were added 4.23 g of (diethylamino)sulfur trifluoride (95%, 24.92 mmol) at 0° C. The reaction mixture was stirred at 0° C. for 35 min. $NaHCO_3$— solution was added and the resulting mixture was extracted with DCM. The combined organic extracts were washed with brine, dried ($MgSO_4$), filtered, and concentrated in vacuo to give a residue which was purified by flash column chromatography (100% pentane) to give 1-bromo-4-(1-fluoro-cyclobutyl)-benzene (3.66 g, 64%) as a colorless liquid.

b) Preparation of 4-(1-fluoro-cyclobutyl)-benzaldehyde

The title compound was synthesized in analogy to 4-cyclopropyl benzaldehyde (described in example S1-A) using 1.64 g of 1-bromo-4-(1-fluoro-cyclobutyl)-benzene (7.16 mmol), 4.92 ml of a 1.6 molar solution of n-BuLi in hexane (7.87 mmol) and 1.1 ml of DMF (14.32 mmol). 4-(1-Fluoro-cyclobutyl)-benzaldehyde was isolated as crude product as a light yellow liquid (1.23 g, 96%). $^{1H}$ NMR ($CDCl_3$, 300 MHz): δ 1.84 (m, 1H), 2.15 (m, 1H), 2.49-2.81 (m, 5H), 7.63 (d, J=8 Hz, 2H), 7.92 (d, J=8 Hz, 2H), 10.03 (s, 1H).

EXAMPLE S4-A

Preparation of 4-(1,2,2,2-tetrafluoro-1-trifluoromethyl-ethyl)-benzaldehyde

A solution of 3.5 g of 4-(heptafluoroisopropyl)-toluene (13.4 mmol) in 100 ml tetrachloromethane was heated to reflux. Then 2.63 g of N-bromosuccinimide (14.8 mmol) and 326 mg of dibenzoyl peroxide (1.34 mmol) were added in small portions. After 5 h the mixture was cooled to 0° C., filtered and the solvent was evaporated. The remaining residue was dissolved in 15 ml ethanol and was added to a suspension that had been prepared by addition of 2-nitropropane (1.4 ml, 15.5 mmol) to a solution of 340 mg sodium (14.8 mmol) in ethanol. This mixture was stirred for 3 days. Then it was filtered, the solvent was removed and the remaining residue was dissolved in EtOAc and washed with 1 N sodium hydroxide solution, 1 N HCl solution, saturated $NaHCO_3$ solution and with brine. The EtOAc layer was then dried with magnesium sulfate, filtered and concentrated. Purification of the residue (silica gel; c-hexane/EtOAc 10:1) gave 1.1 g (30%) of 4-(1,2,2,2-tetrafluoro-1-trifluoromethyl-ethyl)-benzaldehyde as a light yellow oil. $^1H$-NMR ($CDCl_3$, 300 MHz: δ 7.82 (d, J=8 Hz, 2H), 8.03 (d, J=8 Hz, 2H), 10.11 (s, 1H).

EXAMPLE S5-A

Preparation of 4-pentafluoroethyl-benzoic acid a) Preparation of 4-pentafluoroethyl-benzonitrile A mixture of 4-iodobenzonitrile (10.0 g, 43.7 mmol), sodium pentafluoroproprionate (15.4 g, 82.9 mmol), and copper(I) iodide (16.6 g, 87.3 mmol), DMF (160 mL), and toluene (60 mL) was heated at 160° C. for 16 h, allowing most of the toluene to distil off. After cooling, ethyl acetate (200 mL) was added, and the mixture was filtered through diatomaceous earth, and the filtrate was partitioned between ethyl acetate/heptane and water. The organic layer was washed with brine, dried ($MgSO_4$), and evaporated. Chromatography ($SiO_2$, heptane-ethyl acetate gradient) afforded the title compound (5.05 g 52%). Yellow oil, MS (EI) 221.1 ($M^+$).

b) Preparation of 4-pentafluoroethyl-benzoic acid

A mixture of 4-pentafluoroethyl-benzonitrile (2.98 g, 13.5 mmol) and potassium hydroxide (3.03 g, 54.0 mmol) in water (40 mL) and ethanol (20 mL) was heated at reflux for 16 h. After cooling, the solution was partitioned between 1 M aq. hydrochloric acid solution and ethyl acetate. The organic layer was washed with brine, dried ($MgSO_4$), and evaporated.

Chromatography (SiO$_2$, heptane-ethyl acetate gradient) produced the title compound (2.76 g, 85%). White solid, MS (ISP) 238.9 (M−H)$^-$.

EXAMPLE S6-A

Preparation of 4-trimethylsilanyl-benzaldehyde

Bromo-4-(trimethylsilyl)benzene (1.15 g, 5 mmol) was dissolved in THF (30 ml) and cooled to −78° C. Under argon a 1.6 M solution of n-butyl lithium in hexane (3.13 ml, 5 mmol) was added dropwise keeping the temperature below −70° C. The clear colorless solution was stirred at −78° C. for 15 min and DMF (1.156 ml, 15 mmol) was added quickly. The reaction temperature increased to −68° C. The reaction was stirred for additional 15 min at −78° C., quenched with 1N aqueous hydrogen chloride solution and extracted twice with diethyl ether. The combined organic layers were washed twice with water and once with saturated aqueous sodium chloride solution, dried over sodium sulfate, filtered and the solvent was evaporated to leave the product as a colorless oil (920 mg, 100%). The product was pure enough to be used directly in the next step. MS (ISP) 179.2 (M+H$^+$). $^{1H}$ NMR (CDCl$_3$, 300 MHz): δ 10.02 (s, 1H) 7.84 (d, 2H), 7.69 (d, 2H), 0.31 (s, 9H).

EXAMPLE S7-A

Preparation of 4-(1,1-dimethylpropyl)-benzaldehyde

The title compound was synthesized in analogy to example S1-A using 1-bromo-4-(1,1-dimethylpropyl)-benzene (synthesized in analogy to a procedure described in *J. Chem. Res. Miniprint.*, 1997, 12, 2701-2733) (250 mg, 1.10 mmol), nBuLi (825 µl, 1.6M solution in hexane, 1.32 mmol) and DMF (427 µl, 5.50 mmol). The isolated residue was purified by flash column chromatography (1:9 ether:pentane) to give 4-(1,1-dimethylpropyl)-benzaldehyde (175 mg, 90%) as a colorless oil. $^1$H NMR (CDCl$_3$, 300 MHz): 9.99 (s, 1H), 7.82 (d, J=8.5 Hz, 2H), 7.50 (d, J=8.5 Hz, 2H), 1.69 (q, J=7.5 Hz, 2H), 1.32 (s, 6H), 0.68 (t, J=7.5 Hz, 3H).

Primary Amines (Compounds of Formula V)

EXAMPLE S1-B

Preparation of 2-(3-fluoro-5-trifluoromethyl-phenyl)-ethylamine hydrochloride 5.45 g of (3-fluoro-5-trifluoromethyl-phenyl)-acetonitrile (26.3 mmol) were dissolved in 45 ml THF and cooled down to 0° C. under nitrogen. 138 ml borane-tetrahydrofuran complex 1M (138 mmol) were then added dropwise over 20 min by keeping the temperature between 0-2° C. After addition the reaction mixture was stirred at RT for additional 45 min, and refluxed for 17 h. The reaction mixture is then cooled down to 0° C. and treated between 2 and 5° C. with 33 ml methanol over a period of 45 min. After 1 hour refluxing the reaction mixture is concentrated, the residue dissolved in DCM and the amine extrated twice with 1N aqueous HCl. The combined aqueous phases are then treated with concentrated NaOH to adjust the pH to 12, and then extrated twice with DCM. The combined organic phases were then washed with water, dried over magnesium sulfate, filtered and concentrated in vacuo leading to 4.44 g colorless oil. This was dissolved in 100 ml diethylether, treated with 9 ml 2.6N HCl in diethylether, stirred at RT for additional 30 min, filtered and dried under high vacuo, leading to 4.6 g white solid (72%). MS (ISP) 207.1 (M+H)$^+$.

EXAMPLE S2-B

Preparation of 2-(4-chloro-3-trifluoromethyl-phenyl)-ethylamine hydrochloride a) Preparation of (4-chloro-3-trifluoromethyl-phenyl)-acetonitrile 3.94 g of 4-bromomethyl-1-chloro-2-trifluoromethyl-benzene (14.4 mmol) and 1.06 g sodium cyanide (21.6 mmol) were suspended in 12 ml DMSO under argon and stirring and heated to 50° C. for 1 h. The reaction mixture was then poured on water/ice and extracted four times with DCM. The combined organic phases were washed with water, dried with magnesium sulfate, filtered and concentrated in vacuo, leading to 3.188 g of (4-chloro-3-trifluoromethyl-phenyl)-acetonitrile as a dark red oil, which was directly used in the next step.

b) Preparation of 2-(4-chloro-3-trifluoromethyl-phenyl)-ethylamine hydrochloride The title compound was synthesized in analogy to 2-(3-fluoro-5-trifluoromethyl-phenyl)-ethylamine hydrochloride (described in example S1-B) from 3.188 g of crude (4-chloro-3-trifluoromethyl-phenyl)-acetonitrile (14.5 mmol) and 76 ml of a 1M borane-THF complex solution in THF (76 mmol). The product was obtained as a white solid (1.52 g, 40%). MS (ISP) 224.1 (M+H)$^+$.

EXAMPLE S3-B

Preparation of 2-(4-chloro-3-fluoro-phenyl)-ethylamine (S3-B1)

a) Preparation of 1-chloro-2-fluoro-4-(2-nitro-vinyl)-benzene

4-Chloro-3-fluorobenzaldehyde (13 g, 82 mmol) and ammonium acetate (14.6 g, 189 mmol) were dissolved in acetic acid (150 ml) and nitromethane (12.6 ml, 234 mmol) was added. The solution was heated to reflux for 1.5 h. After cooling to RT water (120 ml) was added. A solid precipitated. The reaction was extracted three times with methylene chloride. The combined organic layers were washed with water and sat. aq. NaCl solution, dried over magnesium sulfate, filtered and the solvent was removed in vacuo. The residue was purified by flash column chromatography (Ethyl acetate/cyclohexane:1/4). The crude product was suspended in heptane, filtered and dried to yield 1-chloro-2-fluoro-4-(2-nitro-vinyl)-benzene (10.9 g, 66%) as a light yellow solid. $^{1H}$ NMR (CDCl$_3$, 300 MHz): δ 7.29 (d, J=7.8 Hz, 1H), 7.33 (d, J=9.3 Hz, 1H), 7.50 (t, J=7.5H7, 1H), 7.54 (d, J=13.6 Hz, 1H), 7.92 (d, J=13.6 Hz, 1H).

b) Preparation of 2-(4-chloro-3-fluoro-phenyl)-ethylamine

Lithium borohydride (2.16 g, 99 mmol) was suspended in THF (50 ml). Trimethylchlorosilane (21.6 g, 198 mmol) was added dropwise. A solution of 1-chloro-2-fluoro-4-(2-nitro-vinyl)-benzene (5.0 g, 24.8 mmol) in THF (20 ml) was added dropwise. Strong gas evolution and foam formation was observed. The white suspension was stirred at RT for 3 days. Carefully MeOH (80 ml) was added. The solvents were removed in vacuo and the residue was purified by flash column chromatography (CH$_2$Cl$_2$/MeOH+5% aq. NH$_4$OH 4:1) to yield 2-(4-chloro-3-fluoro-phenyl)-ethylamine (3.1 g, 73%) as a white solid. MS (ISP) 174.1 (M+H)$^+$. $^{1H}$NMR (DMSO-d, 300 MHz): δ 2.92 (t, J=4.8 Hz, 2H), 3.02 (t, J=6.3 Hz, 2H), 7.15 (dd, J=6.0 and 1.2 Hz, 1H), 7.38 (dd, J=1.2 and 7.8 Hz), 7.53 (t, J=6.3 Hz, 1H), 7.93 (br, 2H).

| Example | Name | * | MS (ISP) |
|---|---|---|---|
| S3-B2 | 2-(3-Chloro-5-fluoro-phenyl)-ethylamine hydrochloride | S1-B | 174.0 (M + H)$^+$ |
| S3-B3 | 2-(3-Chloro-4-fluoro-phenyl)-ethylamine hydrochloride | S1-B | 174.1 (M + H)$^+$ |
| S3-B4 | 2-(3-Trifluoromethoxy-phenyl)-ethylamine hydrochloride | S1-B | 206.2 (M + H)$^+$ |
| S3-B5 | 2-(3,5-Dichloro-phenyl)-ethylamine hydrochloride | S3-B | 190.2 (M + H)$^+$ |
| S3-B6 | 2-(3-Chloro-5-trifluoromethyl-phenyl)-ethylamine hydrochloride | S1-B | 222.2 (M + H)$^+$ |
| S3-B7 | 2-(4-Fluoro-3-trifluoromethyl-phenyl)-ethylamine hydrochloride | S1-B | 208.2 (M + H)$^+$ |
| S3-B8 | 2-(3-Benzyloxy-phenyl)-ethylamine hydrochloride | S3-B | 228.4 (M + H)$^+$ |
| S3-B9 | 3-(3-Trifluoromethyl-phenyl)-propylamine hydrochloride | S1-B | 204.1 (M + H)$^+$ |
| S3-B10 | 3-(3-Chloro-phenyl)-propylamine hydrochloride | S1-B | 170.0 (M + H)$^+$ |
| S3-B11 | 3-(4-Chloro-phenyl)-propylamine hydrochloride | S1-B | 170.0 (M + H)$^+$ |
| S3-B12 | 2-(3-Bromo-4-fluoro-phenyl)-ethylamine | S3-B | 201.1 (M + H)$^+$ |

*: Prepared in analogy to example

EXAMPLE S4-B

Preparation of 2-(3-bromo-4-chlorophenyl)-ethylamine a) Preparation of (3-bromo-4-chlorophenyl)-acetonitrile The title compound was synthesized in analogy to example S2-B using 2-bromo-4-bromomethyl-1-chlorobenzene (prepared in analogy to a procedure described in J. Med. Chem.; 2003; 46(20), 4232-4235) (570 mg, 2.00 mmol) and sodium cyanide (147 mg, 3.00 mmol) to give the desired product as a dark red oil which was reacted on without further purification.

b) Preparation of 2-(3-bromo-4-chlorophenyl)-ethylamine

The title compound was synthesized in analogy to example S1-B using crude (3-bromo-4-chlorophenyl)-acetonitrile (475 mg, 2.06 mmol) and 1M borane-THF complex (4.12 ml, 4.12 mmol). The product was obtained as a colorless oil (300 mg, 62%). MS (ISP) 236.0 (M+H)$^+$.

EXAMPLE S5-B

Preparation of 2-(4-chloro-3-ethyl-phenyl)-ethylamine hydrochloride a) Preparation of 4-chloro-3-ethyl-benzaldehyde To a solution of 4.319 g of 4-bromo-1-chloro-2-ethyl-benzene (20 mmol) in 50 ml diethylether, cooled to 0° C., were added dropwise 12.3 ml of 1.6M n-BuLi in hexane. After 30 min. stirring at 0° C. and 2 h at RT, a solution of 2.43 ml DMF (31 mmol) in 10 ml diethylether was added dropwise (temperature raised from 20 to 28° C.). After 1 h additional stirring at RT, the reaction mixture was acidified with 2N HCl, diluted with 150 ml water and extracted with diethylether. The combined organic layers were washed with brine, dried over magnesium sulfate, filtered off and concentrated in vacuo. The residue was purified by flash column chromatography (heptane/AcOEt: 95/5) to yield 2.1 g of a colorless oil. MS (ISP) 168.1 (M+H)$^+$.

b) Preparation of 2-(4-chloro-3-ethyl-phenyl)-ethylamine hydrochloride

The title compound was prepared from 4-chloro-3-ethyl-benzaldehyde in analogy to example S3-B1 steps a) and b). MS (ISP) 184.1 (M+H)$^+$.

EXAMPLE S6-B

Preparation of 2-(4-benzyloxy-3-tert-butyl-phenyl)-ethylamine hydrochloride a) 1-Benzyloxy-2-tert-butyl-4-methyl-benzene 8 g of 2-tert-Butyl-4-methyl-phenol (49 mmol) and 16.36 g of potassium carbonate (58 mmol) were stirred in 120 ml DMF until a suspension was formed. 6.74 ml of benzylchloride were then added dropwise and the reaction mixture was stirred for 24 h at RT. After two hours heating at 60° C., the reaction mixture was cooled to RT, filtered off, diluted with ethyl acetate, and washed with water followed by brine. The organic phase was dried over magnesium sulphate, filtered off and concentrated under vacuo. The residue was purified by flash column chromatography (heptane/AcOEt 98/2) to give 8.647 g of a colorless liquid. MS (ISP) 255.3 (M+H)$^+$.

b) Preparation of 4-benzyloxy-3-tert-butyl-benzaldehyde

A solution of 6.985 g 1-benzyloxy-2-tert-butyl-4-methyl-benzene (27 mmol) and 115 g ammoniumcer (IV)-nitrate in 1000 ml acetic acid (50% v/v) was stirred at 90° C. for one hour. After cooling down to RT, the reaction mixture was extracted with AcOEt/heptane 1:9, dried over magnesium sulfate, filtered off and concentrated under vacuo. The residue was purified by flash column chromatography (heptane/AcOEt 95/5 to 90/10) to give 3.48 g of an orange solid. MS (ISP) 269.3 (M+H)$^+$.

c) Preparation of 2-(4-benzyloxy-3-tert-butyl-phenyl)-ethylamine hydrochloride

The title compound was prepared from 4-benzyloxy-3-tert-butyl-benzaldehyde in analogy to example S3-B1 steps a) and b). MS (ISP) 284.2 (M+H)$^+$.

Secondary Amines (Compounds of Formula III)

EXAMPLE S1-C

Preparation of (4-tert-butyl-benzyl)-[2-(3,4-dichloro-phenyl)-ethyl]-amine 0.38 ml of 4-tert-butylbenzaldehyde (2.25 mmol) and 0.227 ml 2-(3,4-dichloro-phenyl)-ethylamine (1.5 mmol) were dissolved in 4.5 ml methanol at RT, and after stirring for 30 min at RT, were refluxed for 2 h. After cooling down to RT, 85 mg (2.25 mmol) sodium borohydride were added and after stirring for 5 min at RT, the reaction mixture was then refluxed for 2 h. After cooling down to RT, the reaction mixture was treated with 4 drops 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:2) to give 515 mg colorless viscous oil (97%). MS (ISP) 336.2 (M+H)$^+$.

EXAMPLE S2-C

Preparation of (4-tert-butyl-benzyl)-[2-(4-fluoro-3-trifluoromethyl-phenyl)-ethyl]-amine 0.62 ml of 4-tert-butylbenzaldehyde (3.69 mmol), 600 mg of 2-(4-fluoro-3-trifluoro-methyl-phenyl)-ethylamine hydrochloride (2.46 mmol) and 340 mg of potassium carbonate (2.46 mmol) were suspended in 7 ml methanol at RT, and after stirring for 30 min at RT, were refluxed for 2 h. After cooling down to RT, 140 mg (3.69 mmol) of sodium borohydride were added and after stirring for 5 min at RT, the reaction mixture was then refluxed for 3 h. After cooling down to RT, the reaction mixture was treated with 0.5 ml 1 N HCl and concentrated in vacuo. The residue was diluted with water/EtOAc. After separation of the organic phase, the aqueous phase was extracted with EtOAc and the combined organic phases were washed with brine, dried with magnesium sulfate, filtered off and concentrated in vacuo. The residue was purified by column chromatography (40 g silica gel; EtOAc/heptane 1:4 then 1:2) to give 784 mg light yellow oil (90%). MS (ISP) 354.3 (M+H)$^+$.

EXAMPLE S3-C

Preparation of (4-cyclopropylbenzyl)-[2-(3,4-dichlorophenyl)-ethyl]-amine

A mixture of 4-cyclopropyl benzaldehyde (219 mg, 1.50 mmol), 2-(3,4-dichlorophenyl)-ethylamine (284 mg, 1.50 mmol) and molecular sieves (500 mg, 4 Å) in diethyl ether (5 ml) was stirred at RT overnight. The mixture was filtered through celite® and concentrated in vacuo to give the corresponding imine which was dissolved in methanol. Sodium borohydride (85 mg, 2.25 mmol) was added and the reaction mixture was stirred at RT for 4 h. The reaction mixture was then quenched with 0.1N NaOH (aq) and the mixture was diluted with EtOAc and washed with brine. The organic phase was dried (MgSO$_4$), filtered and concentrated in vacuo to give the desired (4-cyclopropylbenzyl)-[2-(3,4-dichlorophenyl)-ethyl]-amine (317 mg, 75%) without further purification as a colorless oil. MS (ISP) 320.2 (M+H)$^+$.

EXAMPLE S4-C

Preparation of (4-tert-butyl-benzyl)-[2-(2-chloro-pyridin-4-yl)-ethyl]-amine a) Preparation of 2-chloro-4-trimethylsilanylethynyl-pyridine A mixture of 2.5 g of 4-bromo-2-chloropyridine (12.6 mmol), 2.2 ml of (trimethylsilyl)acetylene (15.1 mmol), 153 mg of copper(I)iodide (0.79 mmol) and 287 mg of bis(triphenylphosphine)palladium(II)chloride (0.41 mmol) in triethylamine (15 ml) was stirred at RT for 1 h. The triethylamine was then removed in vacuo, water was added and the mixture was extracted with diethylether. The combined organic extracts were then washed with water and brine, dried (Na$_2$SO$_4$), filtered and concentrated in vacuo to give a residue which was purified by column chromatography (heptane/EtOAc 100:0 to 98:2) to give 2-chloro-4-trimethylsilanyl-ethynyl-pyridine (2.394 g, 91%) as a light yellow liquid. MS (ISP) 210.1 (M+H)$^+$.

b) Preparation of 2-chloro-4-ethynyl-pyridine

To a solution of 2.389 g of 2-chloro-4-trimethylsilanyl-ethynyl-pyridine (11.39 mmol) in THF (90 ml) were added 11.39 ml of a 1 M TBAF solution in THF at −78° C. and the reaction mixture was stirred for 45 min at 0° C. Then saturated NH$_4$Cl solution was added and the THF was removed under reduced pressure. The aqueous mixture was extracted with diethylether and the combined organic extracts were washed with water and brine, dried (Na$_2$SO$_4$), filtered and concentrated in vacuo. The remaining residue was purified by column chromatography (pentane/diethylether 100:0 to 4:1) to give 2-chloro-4-ethynyl-pyridine (1.427 g, 91%) as an off-white solid. $^1$H-NMR (CDCl$_3$, 300 MHz: δ 3.36 (s, 1H), 7.27 (dd, J=5 and 1 Hz, 2H), 7.40 (br s, 1H), 8.37 (d, J=8 Hz, 2H).

c) Preparation of (4-tert-butyl-benzyl)-[2-(2-chloro-pyridin-4-yl)-ethyl]-amine

A mixture of 1.386 g of 2-chloro-4-ethynyl-pyridine (10.07 mmol), 2.65 ml of 4-tert-butyl-benzylamine (15.11 mmol), 0.58 ml of acetic acid (10.07 mmol) and 666 mg of sodium cyanoborohydride (95% purity, 10.07 mmol) in ethanol (12 ml) were heated to 105° C. in a sealed tube for 2 d. The reaction mixture was allowed to cool to RT, diluted with 3N NaOH solution and extracted with DCM. The combined organic extracts were washed with saturated NaHCO$_3$ solution and brine, dried (Na$_2$SO$_4$), filtered and concentrated in vacuo. After column chromatography (heptane/EtOAc 100:0 to 0:100) 1.688 g (55%) of the title compound were isolated as a brown liquid. MS (ISP) 303.2 (M+H)$^+$.

EXAMPLE S5-C

Preparation of (4-tert-butylbenzyl)-[2-(4-chloro-3-trifluoromethylpyrazol-1-yl)-ethyl]-amine and (4-tert-butylbenzyl)-[2-(4-chloro-5-trifluoromethylpyrazol-1-yl)-ethyl]-amine a) Preparation of 4-chloro-3-trifluoromethyl-1H-pyrazole To a solution of 3-trifluoromethyl-1H-pyrazole (500 mg, 3.67 mmol) in glacial acetic acid (5 ml) was added a 10% solution of sodium hypochlorite in water (2188 µl, 3.67 mmol). The reaction mixture was stirred at RT overnight and then neutralized with sat. sodium carbonate, and extracted with DCM. The organic layers were combined washed with brine, dried (MgSO$_4$), filtered and concentrated in vacuo to give the desired product (480 mg, 77%) as a white solid which did not require further purification. MS (ISP) 169.0 (M−H)$^−$.

b) Preparation of 2-(4-tert-butylbenzylamino)-ethanol

The title compound was synthesized in analogy to example S3-C using 4-tert-butylbenzaldehyde (1000 mg, 6.17 mmol), ethanolamine (371 µl, 6.17 mmol) and sodium borohydride (350 mg, 9.25 mmol). The desired product (1190 mg, 93%) was isolated without further purification as a colorless oil. MS (ISP) 208.3 (M+H)$^+$.

c) Preparation of 3-(4-tert-butylbenzyl)-[1,2,3]oxathiazolidine 2,2-dioxide

To a solution of 2-(4-tert-butylbenzylamino)-ethanol (1190 mg, 5.74 mmol) and triethylamine (3200 µl, 22.96 mmol) in DCM (15 ml) at −15° C. was added a solution of thionylchloride (544 PI, 7.46 mmol) in DCM (4 ml) over 10 min. The reaction mixture was stirred at −10° C. for 30 min, filtered and the filtrate was concentrated in vacuo. The residue was purified by flash column chromatography to give the desired compound (790 mg, 54%) as a white solid. To a mixture of 3-(4-tert-butylbenzyl)-[1,2,3]oxathiazolidine 2-oxide (790 mg, 3.12 mmol) in DCM (20 ml), acetonitrile (8 ml) and water (8 ml), at 0° C. was added NaIO4 (867 mg, 4.05 mmol) followed by RuO$_2$ (2 mg). The reaction mixture was stirred at 0° C. for 2 h. Water was added and the phases were separated and the aqueous phase was extract with ethyl acetate. The organic layers were combined washed with brine, dried (MgSO$_4$), and concentrated in vacuo. The residue was then purified by flash column chromatography to give the desired product (640 mg, 76%) as an off white solid. MS (ISP) 287.0 (M+NH$_4$)$^+$.

d) Preparation of (4-tert-butylbenzyl)-[2-(4-chloro-3-trifluoromethylpyrazol-1-yl)-ethyl]-amine and (4-tert-butylbenzyl)-[2-(4-chloro-5-trifluoromethylpyrazol-1-yl)-ethyl]-amine To a suspension of NaH (67 mg, 1.67 mmol) in THF (10 ml) at 0° C. was added a solution of 4-chloro-3-trifluoromethyl-1H-pyrazole (190 mg, 1.11 mmol) in THF (5 ml) dropwise. The reaction mixture was stirred at 0° C. for 30 min and then 3-(4-tert-butylbenzyl)-oxathiazolidine 2,2-dioxide (300 mg, 1.11 mmol) was added portion wise. The reaction mixture was warmed to RT and stirred for a further 3 h after which the reaction mixture was quenched with 5 ml 20% (v/v) H$_2$SO$_4$. The reaction mixture was warmed to 60° C. overnight and then cooled to RT and poured into water. The aqueous phase was made basic with 1N NaOH and then extracted with ethyl acetate. The organic layers were combined, washed with brine, dried over MgSO$_4$, filtered and concentrated in vacuo to give a 4:1 mixture of regioisomers (4-tert-butylbenzyl)-[2-(4-chloro-3-trifluoromethylpyrazol-1-yl)-ethyl]-amine (210 mg, 52%) MS (ISP) 360.1 (M+H)$^+$ and (4-tert-butylbenzyl)-[2-(4-chloro-5-trifluoromethylpyrazol-1-yl)-ethyl]-amine (50 mg, 13%) MS (ISP) 360.1 (M+H)$^+$ respectively which were separated by flash column chromatography.

EXAMPLE S6-C

Preparation of (4-tert-butylbenzyl)-[2-(3-cyclopropylphenyl)-ethyl]-amine

To a solution of m-bromophenylcyclopropane (synthesized as described in *J. Org. Chem.* 1976, 41, 2262-2266) (100 mg, 0.51 mmol) in dry THF (3 ml) at −78° C. was added nBuLi (317 µl, 1.6M solution in hexane, 0.51 mmol) dropwise. The reaction mixture was stirred at −78° C. for 10 min and then a solution of 3-(4-tert-butylbenzyl)-[1,2,3]oxathiazolidine 2,2-dioxide (109 mg, 0.41 mmol) in THF (1 ml) was added dropwise. The reaction mixture was warmed to 0° C. over 3 hours and then quenched with 5 ml 20% (v/v) H$_2$SO$_4$. The reaction mixture was warmed to 60° C. overnight and then cooled to RT and poured into water. The aqueous phase was made basic with 1N NaOH and then extracted with ethyl acetate. The organic layers were combined, washed with brine, dried over MgSO$_4$, filtered and concentrated in vacuo to give a crude residue which was purified by flash column chromatography to give (4-tert-butylbenzyl)-[2-(3-cyclopropylphenyl)-ethyl]-amine (72 mg, 58%) as a colorless oil. MS (ISP) 308.4 (M+H)$^+$.

EXAMPLE S7-C

Preparation of (4-tert-butylbenzyl)-[2-(3-chloro-5-cyclopropylphenyl)-ethyl]-amine a) Preparation of 1-bromo-3-chloro-5-cyclopropylbenzene

To a solution of 1,3-dibromo-5-chlorobenzene (500 mg, 1.85 mmol) in THF (1 ml) was added cyclopropylmagnesium bromide (3698 µl, 0.5M solution in THF, 1.85 mmol) in a sealed tube and the reaction mixture was degassed with argon for 5 min before tetrakis(triphenylphosphine)palladium (0) (107 mg, 0.09 mmol) was added. The resulting solution was heated to 70° C. overnight, cooled to RT and then quenched with sat. NH$_4$Cl solution and extracted with pentane. The organic phases were combined, washed with water and brine, dried over MgSO$_4$ and filtered through a short pad of silica gel to give the desired product (272 mg, 64%) which did not require further purification. $^{1H}$ NMR (CDCl$_3$, 300 MHz): 7.28 (aptt, J=2.0 Hz, 1H), 7.08 (aptt, J=1.5 Hz, 1H), 6.97 (aptt, J=1.5 Hz, 1H), 1.83 (m, 1H), 1.04-0.97 (m, 2H), 0.72-0.67 (m, 2H).

b) Preparation of (4-tert-butylbenzyl)-[2-(3-chloro-5-cyclopropylphenyl)-ethyl]-amine The title compound was synthesized in analogy to example S6-C using 1-bromo-3-chloro-5-cyclopropylbenzene (96 mg, 0.71 mmol) and 3-(4-tert-butylbenzyl)-[1,2,3]oxathiazolidine 2,2-dioxide (36 mg, 0.89 mmol). The residue was purified by flash column chromatography to give the desired product (155 mg, 39%) as a colorless oil. MS (ISP) 342.2 (M+H)$^+$.

EXAMPLE S8-C

Preparation of (4-tert-butylbenzyl)-[2-(3-cyclopropyl-4-fluorophenyl)-ethyl]-amine a) Preparation of 3-cyclopropyl-4-fluorophenylamine

To a solution of 3-bromo-4-fluorophenylamine (synthesized as described in *J. Org. Chem.* 1981, 46, 2280-2286)

(415 mg, 2.18 mmol), cyclopropyl boronic acid (244 mg, 2.84 mmol), potassium phosphate (1.62 g, 7.64 mmol), and tricyclohexyl phosphine (61 mg, 0.22 mmol) in toluene (10 ml) and water (0.5 ml) was added palladium acetate (25 mg, 0.11 mmol) and the reaction mixture was heated to 100° C. overnight. The mixture was then cooled to RT and diluted with water and extracted with ether. The organic phases were combined, washed with brine, dried (MgSO$_4$), filtered and concentrated in vacuo to give a residue which was purified by flash column chromatography to give 3-cyclopropyl-4-fluorophenylamine (210 mg, 64%). MS (ISP) 152.2 (M+H)$^+$.

b) Preparation of 2-cyclopropyl-1-fluoro-4-iodobenzene

To a solution of 3-cyclopropyl-4-fluorophenylamine (210 mg, 1.39 mmol) in DME (1.5 ml) was added caesium iodide (360 mg, 1.39 mmol), cuprous iodide (82 mg, 0.43 mmol), iodine (176 mg, 0.70 mmol) and isoamyl nitrite (1.11 ml, 8.34 mmol). The reaction mixture was heated to 60° C. for 2 h. The reaction mixture was cooled to RT and partitioned between pentane and sat. NH$_4$Cl solution. The organic layer was separated, washed with 5% sodium thiosulfite and brine, dried (MgSO$_4$), filtered and concentrated in vacuo to give a residue which was purified by flash column chromatography (100% pentane) to yield the desired 2-cyclopropyl-1-fluoro-4-iodobenzene (262 mg, 72%) as a colorless oil. $^1H$ NMR (CDCl$_3$, 300 MHz): 7.40 (m, 1H), 7.17 (m, 1H), 6.76 (m, 1H), 2.02 (m, 1H), 1.03-0.96 (m, 2H), 0.74-0.68 (m, 2H).

c) Preparation of (4-tert-butylbenzyl)-[2-(3-cyclopropyl-4-fluorophenyl)-ethyl]-amine The title compound was synthesized in analogy to example S6-C using 2-cyclopropyl-1-fluoro-4-iodobenzene (100 mg, 0.38 mmol) and 3-(4-tert-butylbenzyl)-[1,2,3]oxathiazolidine 2,2-dioxide (103 mg, 0.38 mmol). The residue was purified by flash column chromatography to give the desired product (35 mg, 28%) as a colorless oil. MS (ISP) 326.3 (M+H)$^+$.

EXAMPLE S9-C

Preparation of [2-(4-fluoro-phenyl)-ethyl]-(4-pentafluoroethyl-benzyl)-amine (S9-C1)

a) Preparation of N-[2-(4-fluoro-phenyl)-ethyl]-4-pentafluoroethyl-benzamide

A solution of 4-pentafluoroethyl-benzoic acid (500 mg, 2.08 mmol), 2-(4-fluorophenyl)ethylamine (319 mg, 2.29 mmol), 4-methylmorpholine (632 mg, 6.24 mmol), and HBTU (1.19 g, 3.12 mmol) in DMF (38 mL) was stirred at RT for 16 h, then the reaction mixture was partitioned between water and ethyl acetate. The organic layer was washed with brine, dried (MgSO$_4$), and evaporated. Chromatography (SiO$_2$, heptane-ethyl acetate gradient) afforded the title compound (746 mg, 99%). White solid, MS (ISP) 362.2 (M+H)$^+$.

b) Preparation of [2-(4-fluoro-phenyl)-ethyl]-(4-pentafluoroethyl-benzyl)-amine

Borane-tetrahydrofuran complex solution (1 M in THF, 6.5 mL, 6.5 mmol) was added at 0° C. to a solution of N-[2-(4-fluoro-phenyl)-ethyl]-4-pentafluoroethyl-benzamide (740 mg, 2.04 mmol) in THF (8 mL), and the homogeneous solution was heated at reflux over 3 h. After cooling, excess reagent was destroyed by careful addition of methanol at 0° C. Volatile material was removed by distillation, then the residue was dissolved in 5% ethanolic sulfuric acid solution (5 mL). The solution was refluxed for 90 min, then partitioned between 2 M aq. sodium hydroxide solution and ethyl acetate. The organic layer was washed with brine, dried (MgSO$_4$), and evaporated. Chromatography (SiO$_2$, DCM/methanol/NH$_4$OH 95:5:0.1) afforded the title compound (652 mg, 92%). Colorless oil, MS (ISP) 348.2 (M+H)$^+$.

| Example | Name | * | MS (ISP) |
| --- | --- | --- | --- |
| S9-C2 | (4-tert-Butyl-benzyl)-[2-(3-trifluoromethyl-phenyl)-ethyl]-amine | S1-C | 336.3 (M + H)$^+$ |
| S9-C3 | (4-tert-Butyl-benzyl)-phenethyl-amine | S1-C | 268.3 (M + H)$^+$ |
| S9-C4 | (4-tert-Butyl-benzyl)-[2-(3-trifluoromethoxy-phenyl)-ethyl]-amine | S2-C | 352.3 (M + H)$^+$ |
| S9-C5 | (4-tert-Butyl-benzyl)-[2-(4-chloro-3-trifluoromethyl-phenyl)-ethyl]-amine | S2-C | 370.2 (M + H)$^+$ |
| S9-C6 | (4-Cyclobutlylbenzyl)-[2-(3-trifluoromethoxyphenyl)-ethyl]-amine | S2-C | 350.3 (M + H)$^+$ |
| S9-C7 | Butyl-(4-tert-butyl-benzyl)-amine | S1-C | 220.4 (M + H)$^+$ |
| S9-C8 | (4-tert-Butyl-benzyl)-[2-(3-chloro-4-fluoro-phenyl)-ethyl]-amine | S2-C | 320.3 (M + H)$^+$ |
| S9-C9 | [2-(4-Chloro-phenyl)-ethyl]-[4-(1,2,2,2-tetrafluoro-1-trifluoromethyl-ethyl)-benzyl]-amine | S1-C | 414.3 (M + H)$^+$ |
| S9-C10 | (4-Cyclobutyl-benzyl)-[2-(3-trifluoromethyl-phenyl)-ethyl]-amine | S1-C | 334.4 (M + H)$^+$ |
| S9-C11 | (4-Cyclobutyl-benzyl)-[2-(4-fluoro-phenyl)-ethyl]-amine | S1-C | 284.4 (M + H)$^+$ |
| S9-C12 | [2-(4-Chloro-phenyl)-ethyl]-(4-cyclobutyl-benzyl)-amine | S1-C | 300.4 (M + H)$^+$ |
| S9-C13 | (4-tert-Butyl-benzyl)-[2-(4-fluoro-phenyl)-ethyl]-amine | S1-C | 286.2 (M + H)$^+$ |
| S9-C14 | (4-tert-Butyl-benzyl)-[2-(4-chloro-phenyl)-ethyl]-amine | S1-C | 302.3 (M + H)$^+$ |
| S9-C15 | (4-tert-Butyl-benzyl)-[2-(3-chloro-phenyl)-ethyl]-amine | S1-C | 302.3 (M + H)$^+$ |
| S9-C16 | [4-(1-Fluoro-cyclobutyl)-benzyl]-[2-(3-trifluoromethyl-phenyl)-ethyl]-amine | S1-C | 352.4 (M + H)$^+$ |

-continued

| Example | Name | * | MS (ISP) |
|---|---|---|---|
| S9-C17 | [2-(3,4-Dichloro-phenyl)-ethyl]-[4-(1-fluoro-cyclobutyl)-benzyl]-amine | S1-C | 352.3 (M + H)+ |
| S9-C18 | (4-tert-Butyl-benzyl)-[2-(6-trifluoromethyl-pyridin-2-yl)-ethyl]-amine | S4-C | 337.3 (M + H)+ |
| S9-C19 | [2-(4-Chloro-phenyl)-ethyl]-(4-trifluoromethoxy-benzyl)-amine | S1-C | 330.2 (M + H)+ |
| S9-C20 | [2-(4-Chloro-phenyl)-ethyl]-(4-trifluoromethyl-benzyl)-amine | S1-C | 313.9 (M + H)+ |
| S9-C21 | [2-(3-Trifluoromethyl-phenyl)-ethyl]-(4-trimethylsilanyl-benzyl)-amine | S1-C | 352.4 (M + H)+ |
| S9-C22 | [2-(4-Chloro-phenyl)-ethyl]-(4-trimethylsilanyl-benzyl)-amine | S1-C | 318.1 (M + H)+ |
| S9-C23 | [2-(4-Fluoro-phenyl)-ethyl]-(4-trimethylsilanyl-benzyl)-amine | S1-C | 302.2 (M + H)+ |
| S9-C24 | [2-(3,4-Dichloro-phenyl)-ethyl]-(4-trimethylsilanyl-benzyl)-amine | S1-C | 352.3 (M + H)+ |
| S9-C25 | (4-tert-Butyl-benzyl)-[2-(4-chloro-3-fluoro-phenyl)-ethyl]-amine | S1-C | 320.3 (M + H)+ |
| S9-C26 | [2-(3-Trifluoromethoxy-phenyl)-ethyl]-(4-trimethylsilanyl-benzyl)-amine | S1-C | 368.2 (M + H)+ |
| S9-C27 | [2-(4-Chloro-phenyl)-ethyl]-[4-(1-fluoro-cyclobutyl)-benzyl]-amine | S3-C | 318.1 (M + H)+ |
| S9-C28 | [4-(1-Fluoro-cyclobutyl)-benzyl]-[2-(4-fluoro-phenyl)-ethyl]-amine | S3-C | 302.3 (M + H)+ |
| S9-C29 | [2-(3-Chloro-phenyl)-ethyl]-[4-(1-fluoro-cyclobutyl)-benzyl]-amine | S3-C | 318.1 (M + H)+ |
| S9-C30 | [2-(4-Chloro-phenyl)-ethyl]-[4-(1,1-dimethyl-propyl)-benzyl]-amine | S1-C | 316.1 (M + H)+ |
| S9-C31 | [4-(1,1-Dimethyl-propyl)-benzyl]-[2-(3-trifluoromethyl-phenyl)-ethyl]-amine | S3-C | 350.3 (M + H)+ |
| S9-C32 | (4-tert-Butyl-benzyl)-(3-phenyl-propyl)-amine | S1-C | 282.3 (M + H)+ |
| S9-C33 | (4-tert-Butyl-benzyl)-[2-(3-cyclopropyl-5-fluoro-phenyl)-ethyl]-amine | S7-C | 326.2 (M + H)+ |
| S9-C34 | (4-tert-Butyl-benzyl)-[2-(3-chloro-5-fluoro-phenyl)-ethyl]-amine | S2-C | 320.1 (M + H)+ |
| S9-C35 | (4-tert-Butyl-benzyl)-[2-(3-chloro-5-trifluoromethyl-phenyl)-ethyl]-amine | S2-C | 370.0 (M + H)+ |
| S9-C36 | (4-tert-Butyl-benzyl)-[2-(3-fluoro-5-trifluoromethyl-phenyl)-ethyl]-amine | S2-C | 354.3 (M + H)+ |
| S9-C37 | [2-(3,5-Bis-trifluoromethyl-phenyl)-ethyl]-(4-tert-butyl-benzyl)-amine | S1-C | 404.5 (M + H)+ |
| S9-C38 | (4-tert-Butyl-benzyl)-[2-(3,5-dichloro-phenyl)-ethyl]-amine | S1-C | 336.0 (M + H)+ |
| S9-C39 | (4-tert-Butyl-benzyl)-(2-p-tolyl-ethyl)-amine | S1-C | 282.2 (M + H)+ |
| S9-C40 | (4-tert-Butyl-benzyl)-[2-(4-trifluoromethyl-phenyl)-ethyl]-amine | S1-C | 336.2 (M + H)+ |
| S9-C41 | [2-(3-Bromo-phenyl)-ethyl]-(4-tert-butyl-benzyl)-amine | S1-C | 346.1 (M + H)+ |
| S9-C42 | [2-(3-Bromo-4-chlorophenyl)-ethyl]-(4-tert-butylbenzyl)-amine | S3-C | 382.3 (M + H)+ |
| S9-C43 | [2-(3-Benzyloxy-phenyl)-ethyl]-(4-tert-butyl-benzyl)-amine | S2-C | 374.3 (M + H)+ |
| S9-C44 | (4-tert-Butyl-benzyl)-[3-(3-trifluoromethyl-phenyl)-propyl]-amine | S2-C | 350.4 (M + H)+ |
| S9-C45 | (4-tert-Butyl-benzyl)-[2-(4-chloro-3-ethyl-phenyl)-ethyl]-amine | S1-C | 330.4 (M + H)+ |
| S9-C46 | (4-tert-Butyl-benzyl)-[3-(3-chloro-phenyl)-propyl]-amine | S2-C | 316.1 (M + H)+ |
| S9-C47 | (4-tert-Butyl-benzyl)-[3-(4-chloro-phenyl)-propyl]-amine | S2-C | 316.1 (M + H)+ |
| S9-C48 | [2-(4-Benzyloxy-3-tert-butyl-phenyl)-ethyl]-(4-tert-butyl-benzyl)-amine | S2-C | 430.5 (M + H)+ |
| S9-C49 | [2-(3-Bromo-4-fluoro-phenyl)-ethyl]-(4-tert-butyl-benzyl)-amine | S1-C | 366.1 (M + H)+ |

*: Prepared in analogy to example

EXAMPLE S10-C

Preparation of (4-tert-butyl-benzyl)-[2-(3-ethyl-phenyl)-ethyl]-amine a) Preparation of [2-(3-bromo-phenyl)-ethyl]-(4-tert-butyl-benzyl)-carbamic acid tert-butyl ester To a solution of [2-(3-bromo-phenyl)-ethyl]-(4-tert-butyl-benzyl)-amine (3544 mg, 10.23 mmol) in DCM (30 ml) was added di-tert-butyl-dicarbonate (2507 mg, 11.3 mmol) at 0° C. The reaction mixture was stirred for 30 min at 0° C. and then at RT over night. Saturated NH$_4$Cl solution was added and the mixture was extracted with DCM. The combined organic extracts were washed with 10% KHCO$_3$ solution and brine and were dried (Na$_2$SO$_4$). After evaporation of the solvent the crude title compound (4722 mg) was obtained as a colorless oil. MS (ISP) 446.4 (M+H)$^+$.

b) Preparation of (4-tert-butyl-benzyl)-[2-(3-trimethylsilanylethynyl-phenyl)-ethyl]-carbamic acid tert-butyl ester A mixture of the crude [2-(3-bromo-phenyl)-ethyl]-(4-tert-butyl-benzyl)-carbamic acid tert-butyl ester (515 mg, 1.154 mmol), bis(triphenylphosphine)palladium(II)chloride (32 mg, 0.0461 mmol), CuI (11 mg, 0.0577 mmol) and (trimethylsilyl)acetylene (251 µl, 1.73 mmol) in triethylamine (3.4 ml) was heated in a sealed tube at 105° C. over night. The mixture was then cooled to RT, diluted with sat. NaHCO$_3$-solution and extracted three times with ethyl acetate. The combined ethyl acetate layers were then washed with water and brine and were dried (Na$_2$SO$_4$) and evaporated. The remaining residue was purified by chromatography (heptane/EtOAc 100:0 to 95:5) to obtain the title compound as a yellow gum (441 mg, 82%). MS (ISP) 464.4 (M+H)$^+$.

c) Preparation of (4-tert-butyl-benzyl)-[2-(3-ethynyl-phenyl)-ethyl]-carbamic acid tert-butyl ester To a solution of (4-tert-butyl-benzyl)-[2-(3-trimethylsilanylethynyl-phenyl)-ethyl]-carbamic acid tert-butyl ester (440 mg, 0.949 mmol) in THF (7.6 ml) was added a 1 molar solution of TBAF in THF (949 µl, 0.949 mmol) at −78° C. After 15 min at −78° C. the solution was allowed to warm to 0° C. for 30 min. Then brine was added and the mixture was extracted with ether. The combined ether layers were dried (Na$_2$SO$_4$) and evaporated and the remaining residue was purified by chromatography (pentane/ether 100:0 to 90:10) to obtain the title compound as a colorless oil (314 mg, 84%). MS (ISP) 392.3 (M+H)$^+$.

d) Preparation of (4-tert-butyl-benzyl)-[2-(3-ethyl-phenyl)-ethyl]-carbamic acid tert-butyl ester A solution of (4-tert-butyl-benzyl)-[2-(3-ethynyl-phenyl)-ethyl]-carbamic acid tert-butyl ester (149 mg, 0.381 mmol) in methanol (12 ml) was stirred at RT under an atmosphere of hydrogen in the presence of a catalytic amount of palladium on charcoal (5%) for 2 days. The reaction mixture was then filtered and evaporated and the remaining residue was purified by chromatography (heptane/EtOAc 100:0 to 95:5) to obtain the title compound as a colorless oil (73 mg, 48%). MS (ISP) 396.4 (M+H)$^+$.

e) Preparation of (4-tert-butyl-benzyl)-[2-(3-ethyl-phenyl)-ethyl]-amine

To a solution of (4-tert-butyl-benzyl)-[2-(3-ethyl-phenyl)-ethyl]-carbamic acid tert-butyl ester 66 mg, 0.166 mmol) in DCM (1 ml) was added trifluoroacetic acid (128 µl, 1.668 mmol) at 0° C. The reaction mixture was allowed to warm to RT and was stirred over night. The mixture was then basified with 1 N NaOH and extracted with DCM. The combined extracts were dried (Na$_2$SO$_4$) and evaporated to obtain the title compound as a colorless gum (45 mg, 92%). MS (ISP) 296.5 (M+H)$^+$.

EXAMPLE S11-C

Preparation of (4-tert-butylbenzyl)-[2-(4-chloro-3-cyclopropylphenyl)-ethyl]-amine and (4-tert-butyl-benzyl)-[2-(3,4-dicyclopropylphenyl)-ethyl]-amine The title compounds were synthesized in analogy to 3-cyclopropyl-4-fluorophenylamine (step a, example S8-C) using [2-(3-bromo-4-chlorophenyl)-ethyl]-(4-tert-butylbenzyl)-amine (128 mg, 0.34 mmol) and cyclopropyl boronic acid (72 mg, 0.84 mmol). The residue was purified by flash column chromatography to give an unseperable 1:4 mixture of products (4-tert-butylbenzyl)-[2-(4-chloro-3-cyclopropylphenyl)-ethyl]-amine (13 mg, 11%), MS (ISP) 342.2 (M+H)$^+$ and (4-tert-butylbenzyl)-[2-(3,4-dicyclopropylphenyl)-ethyl]-amine (55 mg, 47%), MS (ISP) 348.4 (M+H)$^+$ which was reacted on without further purification.

EXAMPLE S12-C

Preparation of (4-tert-butylbenzyl)-[2-(4-chloro-3-isopropylphenyl)-ethyl]-amine a) Preparation of 2-(5-bromo-2-chlorophenyl)-propan-2-ol

To a solution of 5-bromo-2-chlorobenzoic acid methyl ester (1 g, 4 mmol, 1 eq) in THF (20 ml) at −78° C. was added a 3M solution of methyl magnesium bromide (4 ml, 12 mmol, 3 eq) in THF dropwise. The reaction mixture was then warmed to RT and stirred overnight. The mixture was poured into sat. ammonium chloride solution and extracted with ether. The organic layers were combined, washed with brine, dried (MgSO$_4$), filtered and concentrated in vacuo to give a residue which was purified by flash column chromatography (0 to 20% ether in pentane) to give the desired product as a colorless oil (980 mg, 98%).

b) Preparation of 4-bromo-1-chloro-2-isopropenylbenzene

To a solution of 2-(5-bromo-2-chlorophenyl)-propan-2-ol (500 mg, 2 mmol, 1 eq) in toluene (5 ml) was added a catalytic amount of p-toluenesulfonic acid (38 mg, 0.2 mmol, 0.1 eq) and the solution was refluxed under a Dean-Stark H$_2$O separator overnight. The reaction mixture was allowed to cool to RT and was diluted with ether. The mixture was washed with sat. NaHCO$_3$-solution and brine, dried (MgSO$_4$), filtered and concentrated in vacuo to give the desired product (357 mg, 77%) as a colorless oil which did not require further purification.

c) Preparation of 4-bromo-1-chloro-2-isopropylbenzene

A mixture of 4-bromo-1-chloro-2-isopropenylbenzene (357 mg, 1.54 mmol, 1 eq) and PtO$_2$ (35 mg, 0.15 mmol, 0.1 eq) in 4 ml toluene was stirred under an atmosphere of hydrogen at RT overnight. The reaction mixture was then filtered through celite® and the filtrate was evaporated to dryness to give the desired product (260 mg, 72%). $^{1}H$ NMR (CDCl$_3$, 300 MHz): 7.39 (d, J=2 Hz, 1H), 7.26-7.16 (m, 2H), 3.35 (sept, J=7 Hz, 1H), 1.23 (d, J=7 Hz, 6H).

d) Preparation of (4-tert-butylbenzyl)-[2-(4-chloro-3-isopropylphenyl)-ethyl]-amine The title compound was synthesized in analogy to example S6-C using 4-bromo-1-chloro-2-isopropylbenzene (120 mg, 0.51 mmol), and 3-(4-tert-butylbenzyl)-[1,2,3]oxathiazolidine 2,2-dioxide (138 mg, 0.51 mmol). The residue was purified by flash column chromatography to give the desired product (74 mg, 42%) as a light yellow oil. MS (ISP) 344.3 (M+H)$^+$.

Acids (Compounds of Formula II)

EXAMPLE S1-D

Preparation of
2-chloro-6-trifluoromethyl-isonicotinic acid a) Preparation of
6-chloro-3-iodo-2-trifluoromethyl-pyridine To a stirred solution of 7.1 ml of n-BuLi (1.6M in hexane, 11.3 mmol) in 7 ml THF under argon at −73° C. were added 1.6 ml of diisopropylamine (11.3 mmol) in 3 ml THF within 8 min. After 10 min stirring at the same temperature a solution of 1 g of 2-chloro-6-(trifluoromethyl)-pyridine (5.51 mmol) in 5 ml THF was added within 15 min (temperature between −76 and −75° C.). The dark brown solution was stirred at −75° C. for 1 h 15 min. Finally a solution of 1.4 g of iodine (5.51 mmol) in 10 ml THF was added at −75° C. over 25 min. After additional 45 min stirring at the same temperature 12 ml 2M aqueous HCl were added within 2 min (temperature raised from −78 to −50° C. The cooling device was then removed, the reaction mixture diluted with diethylether. After separation of the organic phase, the aqueous phase was reextracted with diethylether. The combined organic phases were successively washed with 10 ml 1M sodium thiosulfate, saturated NaHCO$_3$ and brine, dried over magnesium sulfate, filtered off and concentrated in vacuo to yield 1.54 (69%) of 6-chloro-3-iodo-2-trifluoromethyl-pyridine as a brown semisolid residue. MS: 307.0 b) Preparation of
2-chloro-4-iodo-6-trifluoromethyl-pyridine

To a stirred solution of 3.05 ml of n-BuLi (1.6 M in hexane, 4.88 mmol) under argon at −75° C. was added 0.69 ml of diisopropylamine (4.88 mmol) in 2.5 ml THF over 5 min (temperature between −72 and −75° C.). After 10 min at −75° C. a solution of 1.5 g of 6-chloro-3-iodo-2-trifluoromethyl-pyridine (4.88 mmol) in 3.5 ml THF was added dropwise over 20 min at the same temperature. After 1.5 hours stirring at −75° C., 6 ml 2M aqueous HCl were added (temperature was allowed to raise to RT). The mixture was then diluted with water, extracted with diethylether and the combined organic phases were successively washed with saturated NaHCO$_3$ solution and brine, dried over magnesium sulfate, filtered off and concentrated in vacuo. The residue was purified by silicagel chromatography (eluent:heptane/AcOEt 95:5) leading to 1.145 g (69%) of 2-chloro-4-iodo-6-trifluoromethyl-pyridine as a white powder. MS: 307.0 c) Preparation of
2-chloro-6-trifluoromethyl-isonicotinic acid

To a stirred solution of 1.1 g of 2-chloro-4-iodo-6-trifluoromethyl-pyridine (3.58 mmol) in 15 ml THF under argon at −75° C., were added 2.2 ml of n-BuLi (1.6 M in hexane) within 15 min (temperature kept between −72° C. and −75° C.). After 5 additional min stirring at −75° C., the reaction mixture was poured on an excess of freshly crushed dry ice and stirred until RT was reached. The reaction mixture was then concentrated in vacuo, the remaining residue treated with 2M aqueous HCl and the resulting mixture was extrated with diethylether. The combined organic phases were washed with water, and then extracted with saturated NaHCO$_3$ solution. The aqueous phase was then acidified with concentrated HCl, extracted twice with diethylether and the combined organic phases were washed with brine, dried over magnesium sulfate, filtered and concentrated in vacuo. The remaining residue was recrystalized from 12 ml hot n-hexane, leading to 0.459 g (56%) of 2-chloro-6-trifluoromethyl-isonicotinic acid as an off-white solid. MS: 224.0 (M−H)$^-$.

EXAMPLE S2-D

Preparation of
3-chloro-4-fluoro-5-trifluoromethyl-benzoic acid

To a stirred solution of 2.03 ml of sec-BuLi (1.3M in cyclohexane, 2.64 mmol) and 0.4 ml of TMEDA under argon at −90° C. was added a solution of 0.25 g of 4-fluoro-3-trifluoromethyl-benzoic acid (1.2 mmol) in 8 ml THF over 20 min (temperature kept between −92° C. and −88° C.). After 30 min stirring at the same temperature, the initially light orange suspension turned brown. A solution of 1.14 g of hexachloroethane (4.82 mmol) in 10 ml THF was then added within 2 min (temperature raised to −62° C.). The reaction mixture was then left to warm slowly to RT (1 hour) and treated carefully with 2 ml water. The reaction mixture was then concentrated in vacuo, diluted with water and extracted with diethylether. The aqueous phase was then acidified with concentrated HCl and extrated twice with ethylacetate. The combined ethylacetate phases were subsequently washed with water (3×) and brine (1×), dried over magnesium sulfate, filtered and concentrated in vacuo to yield 0.28 g of a residue which was purified by silicagel chromatography (eluent heptane/AcOEt 90:10 to 75:25) to yield 22 mg of 3-chloro-4-fluoro-5-trifluoromethyl-benzoic acid as a light yellow solid. MS: 241.1 (M−H)$^-$.

EXAMPLE S3-D

Preparation of 3-chloro-5-cyclopropylbenzoic acid

To a solution of 1-bromo-3-chloro-5-cyclopropylbenzene (300 mg, 1.30 mmol) at −78° C. in THF (5 ml) was added nBuLi (890 μl, 1.6M solution in hexane, 1.43 mmol) dropwise. The resulting solution was stirred at −78° C. for 10 min after which solid carbon dioxide was added and the reaction mixture was warmed to RT over 3 hours. The reaction mixture was quenched with water and then extracted with ether. The aqueous phase was then made acidic with 1N HCl and then extracted with ethyl acetate. The organic phases were combined, washed with brine, dried (MgSO$_4$), filtered and concentrated in vacuo to give the desired product 3-chloro-5- cyclopropylbenzoic acid (178 mg, 70%) which did not require further purification. MS (ISP) 195.1 (M–H)⁻.

EXAMPLE S4-D

Preparation of 6-chloro-4-trifluoromethyl-pyridine-2-carboxylic acid

To a solution of 300 mg of 2-chloro-6-methyl-4-(trifluoromethyl)-pyridine (1.49 mmol) in pyridine (5 ml) was added a solution of 1.61 g of tetrabutylammonium permanganate (4.46 mmol) in pyridine (4.5 ml) and the reaction mixture was stirred at 80° C. for 3 h. The reaction mixture was then poured into a mixture of water and ice and then NaHSO$_3$ solution (40% in water) was added until the color turned light yellow. The mixture was then acidified by addition of 2N HCl and extracted with ethyl acetate. The combined organic layers were then washed with 1N HCl and brine, dried (Na$_2$SO$_4$), filtered and concentrated. The remaining residue was purified by chromatography (DCM/MeOH 100:0 to 90:10) to yield 224 mg (67%) of a gray liquid. MS (ISP) 224.3 (M–H)⁻.

EXAMPLE S5-D

Preparation of 6-Methyl-2-trifluoromethyl-pyrimidine-4-carboxylic acid a) Preparation of 6-methyl-2-trifluoromethyl-pyrimidine-4-carboxylic acid ethyl ester 2.241 g (20 mmol) of 2,2,2-trifluoro-acetamidine were dissolved in 80 ml ethanol and treated with 3.163 g (20 mmol) of 2,4-dioxo-pentanoic acid ethyl ester. The resulting solution was cooled to 0-5° C. and treated with 120 ml of HCl-saturated ethanol. The reaction mixture was allowed to warm-up to RT and stirred for additional 3 hours. The mixture was then added dropwise under cooling to 800 ml saturated NaHCO$_3$ solution. The resulting mixture was then extracted twice with 300 ml DCM and the combined organic phases were dried over magnesium sulfate, filtered and concentrated in vacuo to yield 3.1 g of a yellow oil. This residue was then purified by silicagel chromatography (eluent:heptane/ethyl acetate 100:0 to 30:70) leading to a colorless oil which crystallized spontaneously, leading to 1.3 g of 6-methyl-2-trifluoromethyl-pyrimidine-4-carboxylic acid ethyl ester.

b) Preparation of 6-methyl-2-trifluoromethyl-pyrimidine-4-carboxylic acid 1.3 g (5.551 mmol) of 6-methyl-2-trifluoromethyl-pyrimidine-4-carboxylic acid ethyl ester were dissolved in 30 ml dioxane and treated with 11.1 ml (11.1 mmol) 1 N NaOH and stirred for 2 hours at RT. The reaction mixture was then treated with 11.1 ml (11.1 mmol) 1 N HCl and concentrated in vacuo. The resulting solid residue was then suspended in DCM-methanol, filtered-off, washed with additional DCM-methanol and the combined organic phases were then concentrated in vacuo, to yield 1.1 g (96%) of 6-methyl-2-trifluoromethyl-pyrimidine-4-carboxylic acid. MS: 205.1 (M–H)⁻.

Compounds of Formula I

EXAMPLE 1

Preparation of N-(4-tert-butyl-benzyl)-3-chloro-N-[2-(4-chloro-phenyl)-ethyl]-2-fluoro-5-trifluoromethyl-benzamide (B1)

To a solution of 50 mg of 3-chloro-2-fluoro-5-trifluoromethyl-benzoic acid (0.206 mmol) and 68 mg (0.225 mmol) of (4-tert-butylbenzyl)-[2-(4-chlorophenyl)-ethyl]-amine in 3 ml of DMF were added 117 mg of HBTU (0.31 mmol) and 0.063 ml (0.62 mmol) of 4-methylmorpholine. After stirring the reaction mixture over night at RT it was poured on a mixture of 15 ml of brine and 15 ml of water and extracted with ethyl acetate. The combined organic phases were washed with brine, dried with magnesium sulfate, filtered and concentrated in vacuo. The residue was purified by column chromatography (silica gel; heptane/EtOAc 95:5) to give 76 mg (70%) of a light yellow amorphous material. MS (ISP) 526.0 (M+H)⁺. In analogy to example 1:

| Example | Name | MS |
| --- | --- | --- |
| B2 | N-(4-tert-Butyl-benzyl)-N-[2-(3,4-dichloro-phenyl)-ethyl]-2-fluoro-nicotinamide | 459.3 [ISP(M + H)+] |
| B3 | N-(4-tert-Butyl-benzyl)-4-chloro-N-[2-(3,4-dichloro-phenyl)-ethyl]-nicotinamide | 475.2 [ISP(M + H)+] |
| B4 | N-(4-tert-Butyl-benzyl)-2,5-dichloro-N-[2-(3,4-dichloro-phenyl)-ethyl]-nicotinamide | 509 [ISP(M + H)+] |
| B5 | 5-Bromo-N-(4-tert-butyl-benzyl)-2-chloro-N-[2-(3,4-dichloro-phenyl)-ethyl]-nicotinamide | 553 [ISP(M + H)+] |
| B6 | N-(4-tert-Butyl-benzyl)-2-chloro-N-[2-(3,4-dichloro-phenyl)-ethyl]-5-fluoro-nicotinamide | 493.3 [ISP(M + H)+] |
| B7 | N-(4-tert-Butyl-benzyl)-2-chloro-N-[2-(3,4-dichloro-phenyl)-ethyl]-5-trifluoromethyl-isonicotinamide | 543.1 [ISP(M + H)+] |
| B8 | N-(4-tert-Butoxy-benzyl)-3-chloro-2-fluoro-5-trifluoromethyl-N-[2-(3-trifluoromethyl-phenyl)-ethyl]-benzamide | 576.1 [ISP(M + H)+] |
| B9 | N-(4-tert-Butyl-benzyl)-2,6-dichloro-N-[2-(3-trifluoromethyl-phenyl)-ethyl]-isonicotinamide | 509.3 [ISP(M + H)+] |
| B10 | N-(4-tert-Butyl-benzyl)-2,6-dichloro-N-[2-(3-fluoro-5-trifluoromethyl-phenyl)-ethyl]-isonicotinamide | 527 [ISP(M + H)+] |
| B11 | N-(4-tert-Butyl-benzyl)-2,6-dichloro-N-[2-(4-fluoro-3-trifluoromethyl-phenyl)-ethyl]-isonicotinamide | 527 [ISP(M + H)+] |

-continued

| Example | Name | MS |
|---|---|---|
| B12 | N-(4-tert-Butyl-benzyl)-2-chloro-N-[2-(3-fluoro-5-trifluoromethyl-phenyl)-ethyl]-6-trifluoromethyl-isonicotinamide | 561.3 [ISP(M + H)+] |
| B13 | N-(4-tert-Butyl-benzyl)-2,6-dichloro-N-[2-(3-chloro-5-trifluoromethyl-phenyl)-ethyl]-isonicotinamide | 543.1 [ISP(M + H)+] |
| B14 | N-(4-tert-Butyl-benzyl)-2-chloro-N-[2-(3-chloro-5-trifluoromethyl-phenyl)-ethyl]-6-trifluoromethyl-isonicotinamide | 577.2 [ISP(M + H)+] |
| B15 | N-(4-tert-Butyl-benzyl)-2-chloro-6-trifluoromethyl-N-[2-(3-trifluoromethyl-phenyl)-ethyl]-isonicotinamide | 543.1 [ISP(M + H)+] |
| B16 | N-(4-tert-Butyl-benzyl)-2-chloro-N-[2-(4-fluoro-3-trifluoromethyl-phenyl)-ethyl]-6-trifluoromethyl-isonicotinamide | 561.3 [ISP(M + H)+] |
| B17 | N-(4-tert-Butyl-benzyl)-2,6-dichloro-N-[2-(4-chloro-3-fluoro-phenyl)-ethyl]-isonicotinamide | 493.1 [ISP(M + H)+] |
| B18 | N-(4-tert-Butyl-benzyl)-2-chloro-N-[2-(3,4-dichloro-phenyl)-ethyl]-6-trifluoromethyl-isonicotinamide | 543.2 [ISP(M + H)+] |
| B19 | N-(4-tert-Butyl-benzyl)-3-chloro-N-[2-(2-chloro-pyridin-4-yl)-ethyl]-5-trifluoromethyl-benzamide | 509.4 [ISP(M + H)+] |
| B20 | N-(4-tert-Butyl-benzyl)-3-chloro-N-[2-(2-chloro-pyridin-4-yl)-ethyl]-2-fluoro-5-trifluoromethyl-benzamide | 527.1 [ISP(M + H)+] |
| B21 | N-(4-tert-Butyl-benzyl)-3-chloro-N-[2-(4-chloro-3-trifluoromethyl-pyrazol-1-yl)-ethyl]-5-trifluoromethyl-benzamide | 566.2 [ISP(M + H)+] |
| B22 | N-(4-tert-Butyl-benzyl)-3-chloro-N-[2-(4-chloro-3-trifluoromethyl-pyrazol-1-yl)-ethyl]-2-fluoro-5-trifluoromethyl-benzamide | 584.1 [ISP(M + H)+] |
| B23 | N-(4-tert-Butyl-benzyl)-3-chloro-5-trifluoromethyl-N-[2-(6-trifluoromethyl-pyridin-2-yl)-ethyl]-benzamide | 543.1 [ISP(M + H)+] |
| B24 | N-(4-tert-Butyl-benzyl)-3-chloro-2-fluoro-5-trifluoromethyl-N-[2-(6-trifluoromethyl-pyridin-2-yl)-ethyl]-benzamide | 561 [ISP(M + H)+] |
| B25 | N-(4-tert-Butyl-benzyl)-3-chloro-2-fluoro-N-phenethyl-5-trifluoromethyl-benzamide | 492 [ISP(M + H)+] |
| B26 | N-(4-tert-Butyl-benzyl)-3-chloro-N-[2-(3,4-dichloro-phenyl)-ethyl]-2-fluoro-5-trifluoromethyl-benzamide | 559.8 [ISP(M + H)+] |
| B27 | N-(4-tert-Butyl-benzyl)-3-chloro-2-fluoro-N-(2-p-tolyl-ethyl)-5-trifluoromethyl-benzamide | 506 [ISP(M + H)+] |
| B28 | N-(4-tert-Butyl-benzyl)-3-chloro-2-fluoro-N-[2-(4-fluoro-phenyl)-ethyl]-5-trifluoromethyl-benzamide | 510.3 [ISP(M + H)+] |
| B29 | N-(4-tert-Butyl-benzyl)-3-chloro-N-[2-(3-chloro-phenyl)-ethyl]-2-fluoro-5-trifluoromethyl-benzamide | 526.1 [ISP(M + H)+] |
| B30 | N-(4-tert-Butyl-benzyl)-3-chloro-2-fluoro-5-trifluoromethyl-N-[2-(3-trifluoromethyl-phenyl)-ethyl]-benzamide | 560.3 [ISP(M + H)+] |
| B31 | N-(4-tert-Butyl-benzyl)-3-chloro-N-[2-(3,4-dichloro-phenyl)-ethyl]-2-fluoro-benzamide | 492.2 [ISP(M + H)+] |
| B32 | N-(4-tert-Butyl-benzyl)-3-chloro-2-fluoro-N-[2-(3-trifluoromethyl-phenyl)-ethyl]-benzamide | 491.3 [ISP(M + H)+] |
| B33 | N-(4-tert-Butyl-benzyl)-3,5-bis-trifluoromethyl-N-[2-(3-trifluoromethyl-phenyl)-ethyl]-benzamide | 576.1 [ISP(M + H)+] |
| B34 | N-(4-tert-Butyl-benzyl)-2,6-difluoro-3-trifluoromethyl-N-[2-(3-trifluoromethyl-phenyl)-ethyl]-benzamide | 544.3 [ISP(M + H)+] |
| B35 | N-(4-tert-Butyl-benzyl)-2,4,6-trifluoro-N-[2-(3-trifluoromethyl-phenyl)-ethyl]-benzamide | 494.5 [ISP(M + H)+] |
| B36 | N-(4-tert-Butyl-benzyl)-2-fluoro-5-iodo-N-[2-(3-trifluoromethyl-phenyl)-ethyl]-benzamide | 584.2 [ISP(M + H)+] |
| B37 | N-(4-tert-Butyl-benzyl)-5-chloro-2,3,4-trifluoro-N-[2-(3-trifluoromethyl-phenyl)-ethyl]-benzamide | 528.3 [ISP(M + H)+] |
| B38 | N-(4-tert-Butyl-benzyl)-3-chloro-2-fluoro-5-hydroxy-N-[2-(3-trifluoromethyl-phenyl)-ethyl]-benzamide | 508.5 [ISP(M + H)+] |
| B39 | N-(4-tert-Butyl-benzyl)-5-chloro-2-fluoro-N-[2-(3-trifluoromethyl-phenyl)-ethyl]-benzamide | 492.1 [ISP(M + H)+] |
| B40 | N-(4-tert-Butyl-benzyl)-3,5-dichloro-2-hydroxy-N-[2-(3-trifluoromethyl-phenyl)-ethyl]-benzamide | 523.2 [ISP(M + H)+] |
| B41 | N-(4-tert-Butyl-benzyl)-3-chloro-2-fluoro-N-[2-(3-trifluoromethoxy-phenyl)-ethyl]-5-trifluoromethyl-benzamide | 576.1 [ISP(M + H)+] |
| B42 | N-(4-tert-Butyl-benzyl)-2,5-dichloro-N-[2-(3-trifluoromethyl-phenyl)-ethyl]-benzamide | 508.3 [ISP(M + H)+] |
| B43 | N-(4-tert-Butyl-benzyl)-5-chloro-2-trifluoromethyl-N-[2-(3-trifluoromethyl-phenyl)-ethyl]-benzamide | 542.2 [ISP(M + H)+] |

-continued

| Example | Name | MS |
|---|---|---|
| B44 | N-(4-tert-Butyl-benzyl)-3-chloro-5-fluoro-N-[2-(3-trifluoromethyl-phenyl)-ethyl]-benzamide | 492.1 [ISP(M + H)+] |
| B45 | N-(4-tert-Butyl-benzyl)-3,5-dichloro-N-[2-(3-trifluoromethyl-phenyl)-ethyl]-benzamide | 508.3 [ISP(M + H)+] |
| B46 | N-(4-tert-Butyl-benzyl)-3-fluoro-5-trifluoromethyl-N-[2-(3-trifluoromethyl-phenyl)-ethyl]-benzamide | 526.3 [ISP(M + H)+] |
| B47 | N-(4-tert-Butyl-benzyl)-2,3-dichloro-N-[2-(3-trifluoromethyl-phenyl)-ethyl]-benzamide | 508.3 [ISP(M + H)+] |
| B48 | N-(4-tert-Butyl-benzyl)-3-chloro-5-trifluoromethyl-N-[2-(3-trifluoromethyl-phenyl)-ethyl]-benzamide | 542.2 [ISP(M + H)+] |
| B49 | N-(4-tert-Butyl-benzyl)-3,5-dichloro-N-[2-(3-trifluoromethoxy-phenyl)-ethyl]-benzamide | 524.1 [ISP(M + H)+] |
| B50 | N-(4-tert-Butyl-benzyl)-3,5-dichloro-N-[2-(4-fluoro-phenyl)-ethyl]-benzamide | 458.2 [ISP(M + H)+] |
| B51 | N-(4-tert-Butyl-benzyl)-3-chloro-N-[2-(3-trifluoromethoxy-phenyl)-ethyl]-5-trifluoromethyl-benzamide | 558.2 [ISP(M + H)+] |
| B52 | N-(4-tert-Butyl-benzyl)-3-chloro-N-[2-(4-fluoro-phenyl)-ethyl]-5-trifluoromethyl-benzamide | 492.1 [ISP(M + H)+] |
| B53 | N-(4-tert-Butyl-benzyl)-3-chloro-N-[2-(4-chloro-phenyl)-ethyl]-5-trifluoromethyl-benzamide | 508.3 [ISP(M + H)+] |
| B54 | N-(4-tert-Butyl-benzyl)-3-fluoro-N-[2-(3-trifluoromethoxy-phenyl)-ethyl]-5-trifluoromethyl-benzamide | 542.2 [ISP(M + H)+] |
| B55 | N-(4-tert-Butyl-benzyl)-N-[2-(4-chloro-phenyl)-ethyl]-3-fluoro-5-trifluoromethyl-benzamide | 492.1 [ISP(M + H)+] |
| B56 | N-(4-tert-Butyl-benzyl)-3,5-dimethyl-N-[2-(3-trifluoromethyl-phenyl)-ethyl]-benzamide | 468.5 [ISP(M + H)+] |
| B57 | N-(4-tert-Butyl-benzyl)-2-fluoro-5-trifluoromethyl-N-[2-(3-trifluoromethyl-phenyl)-ethyl]-benzamide | 526.3 [ISP(M + H)+] |
| B58 | N-(4-tert-Butyl-benzyl)-3-chloro-4-fluoro-5-trifluoromethyl-N-[2-(3-trifluoromethyl-phenyl)-ethyl]-benzamide | 560.3 [ISP(M + H)+] |
| B59 | N-(4-tert-Butyl-benzyl)-3-chloro-N-[2-(3-fluoro-5-trifluoromethyl-phenyl)-ethyl]-5-trifluoromethyl-benzamide | 560.3 [ISP(M + H)+] |
| B60 | N-(4-tert-Butyl-benzyl)-3-chloro-N-[2-(4-fluoro-3-trifluoromethyl-phenyl)-ethyl]-5-trifluoromethyl-benzamide | 560.3 [ISP(M + H)+] |
| B61 | N-(4-tert-Butyl-benzyl)-4-chloro-3-trifluoromethyl-N-[2-(3-trifluoromethyl-phenyl)-ethyl]-benzamide | 542.1 [ISP(M + H)+] |
| B62 | N-(4-tert-Butyl-benzyl)-3-chloro-N-[2-(3,4-dichloro-phenyl)-ethyl]-5-trifluoromethyl-benzamide | 542.2 [ISP(M + H)+] |
| B63 | N-(4-tert-Butyl-benzyl)-3-chloro-2-fluoro-N-[2-(3-fluoro-5-trifluoromethyl-phenyl)-ethyl]-5-trifluoromethyl-benzamide | 578.3 [ISP(M + H)+] |
| B64 | N-(4-tert-Butyl-benzyl)-3-fluoro-N-[2-(3-fluoro-5-trifluoromethyl-phenyl)-ethyl]-5-trifluoromethyl-benzamide | 544.3 [ISP(M + H)+] |
| B65 | N-(4-tert-Butyl-benzyl)-3-chloro-2-fluoro-N-[2-(4-fluoro-3-trifluoromethyl-phenyl)-ethyl]-5-trifluoromethyl-benzamide | 578.2 [ISP(M + H)+] |
| B66 | N-(4-tert-Butyl-benzyl)-3-chloro-N-(3-phenyl-propyl)-5-trifluoromethyl-benzamide | 488.1 [ISP(M + H)+] |
| B67 | N-(4-tert-Butyl-benzyl)-3,5-dichloro-4-fluoro-N-[2-(3-trifluoromethyl-phenyl)-ethyl]-benzamide | 526.2 [ISP(M + H)+] |
| B68 | N-(4-tert-Butyl-benzyl)-3,5-dichloro-N-[2-(3-fluoro-5-trifluoromethyl-phenyl)-ethyl]-benzamide | 526 [ISP(M + H)+] |
| B69 | N-(4-tert-Butyl-benzyl)-3,5-dichloro-N-[2-(4-fluoro-3-trifluoromethyl-phenyl)-ethyl]-benzamide | 526 [ISP(M + H)+] |
| B70 | N-(4-tert-Butyl-benzyl)-3,5-dichloro-4-fluoro-N-[2-(3-fluoro-5-trifluoromethyl-phenyl)-ethyl]-benzamide | 544.1 [ISP(M + H)+] |
| B71 | N-(4-tert-Butyl-benzyl)-3,5-dichloro-N-[2-(3,4-dichloro-phenyl)-ethyl]-benzamide | 508.2 [ISP(M + H)+] |
| B72 | N-(4-tert-Butyl-benzyl)-3-chloro-N-[2-(3-cyclopropyl-phenyl)-ethyl]-5-trifluoromethyl-benzamide | 514.2 [ISP(M + H)+] |
| B73 | N-(4-tert-Butyl-benzyl)-3-chloro-N-[2-(3-chloro-5-cyclopropyl-phenyl)-ethyl]-5-trifluoromethyl-benzamide | 548.1 [ISP(M + H)+] |
| B74 | N-(4-tert-Butyl-benzyl)-3-chloro-N-[2-(3-chloro-5-cyclopropyl-phenyl)-ethyl]-2-fluoro-5-trifluoromethyl-benzamide | 566.2 [ISP(M + H)+] |
| B75 | N-(4-tert-Butyl-benzyl)-3-chloro-N-[2-(3-cyclopropyl-5-fluoro-phenyl)-ethyl]-2-fluoro-5-trifluoromethyl-benzamide | 550.2 [ISP(M + H)+] |

-continued

| Example | Name | MS |
|---|---|---|
| B76 | N-(4-tert-Butyl-benzyl)-3-chloro-5-cyclopropyl-N-[2-(3-fluoro-5-trifluoromethyl-phenyl)-ethyl]-benzamide | 532.1 [ISP(M + H)+] |
| B77 | N-(4-tert-Butyl-benzyl)-3-chloro-5-cyclopropyl-N-[2-(3-trifluoromethyl-phenyl)-ethyl]-benzamide | 514.2 [ISP(M + H)+] |
| B78 | N-(4-tert-Butyl-benzyl)-3-chloro-N-[2-(3-chloro-5-trifluoromethyl-phenyl)-ethyl]-2-fluoro-5-trifluoromethyl-benzamide | 594.2 [ISP(M + H)+] |
| B79 | N-(4-tert-Butyl-benzyl)-3-chloro-N-[2-(3-chloro-5-trifluoromethyl-phenyl)-ethyl]-5-trifluoromethyl-benzamide | 576.3 [ISP(M + H)+] |
| B80 | N-(4-tert-Butyl-benzyl)-3-chloro-N-[2-(4-chloro-3-fluoro-phenyl)-ethyl]-5-trifluoromethyl-benzamide | 526 [ISP(M + H)+] |
| B81 | 3-Chloro-N-[2-(4-chloro-phenyl)-ethyl]-2-fluoro-N-[4-(1,2,2,2-tetrafluoro-1-trifluoromethyl-ethyl)-benzyl]-5-trifluoromethyl-benzamide | 638.1 [ISP(M + H)+] |
| B82 | 3-Chloro-2-fluoro-N-[2-(4-fluoro-phenyl)-ethyl]-N-(4-pentafluoroethyl-benzyl)-5-trifluoromethyl-benzamide | 572.1 [ISP(M + H)+] |
| B83 | N-(4-tert-Butyl-benzyl)-2-chloro-5-trifluoromethyl-N-[2-(3-trifluoromethyl-phenyl)-ethyl]-benzamide | 542.3 [ISP(M + H)+] |
| B84 | N-(4-tert-Butyl-benzyl)-3,5-difluoro-N-[2-(3-trifluoromethyl-phenyl)-ethyl]-benzamide | 476 [ISP(M + H)+] |
| B85 | N-(4-tert-Butyl-benzyl)-3,5-dichloro-N-[2-(4-chloro-phenyl)-ethyl]-benzamide | 474 [ISP(M + H)+] |
| B86 | N-(4-tert-Butyl-benzyl)-3-chloro-2-fluoro-5-trifluoromethyl-N-[2-(4-trifluoromethyl-phenyl)-ethyl]-benzamide | 560.3 [ISP(M + H)+] |
| B87 | N-(4-tert-Butyl-benzyl)-3-fluoro-N-[2-(4-fluoro-phenyl)-ethyl]-5-trifluoromethyl-benzamide | 476 [ISP(M + H)+] |
| B88 | 3-Chloro-N-(4-cyclobutyl-benzyl)-2-fluoro-N-[2-(3-trifluoromethoxy-phenyl)-ethyl]-5-trifluoromethyl-benzamide | 574.3 [ISP(M + H)+] |
| B89 | 3-Chloro-N-(4-cyclobutyl-benzyl)-N-[2-(3-trifluoromethoxy-phenyl)-ethyl]-5-trifluoromethyl-benzamide | 556.2 [ISP(M + H)+] |
| B90 | N-(4-Cyclobutyl-benzyl)-3-fluoro-N-[2-(3-trifluoromethoxy-phenyl)-ethyl]-5-trifluoromethyl-benzamide | 540.3 [ISP(M + H)+] |
| B91 | 3,5-Dichloro-N-(4-cyclobutyl-benzyl)-N-[2-(3-trifluoromethoxy-phenyl)-ethyl]-benzamide | 552.3 [ISP(M + H)+] |
| B92 | 3-Chloro-N-(4-cyclobutyl-benzyl)-2-fluoro-5-trifluoromethyl-N-[2-(3-trifluoromethyl-phenyl)-ethyl]-benzamide | 558 [ISP(M + H)+] |
| B93 | 3-Chloro-N-(4-cyclobutyl-benzyl)-5-trifluoromethyl-N-[2-(3-trifluoromethyl-phenyl)-ethyl]-benzamide | 540.2 [ISP(M + H)+] |
| B94 | N-(4-Cyclobutyl-benzyl)-3-fluoro-5-trifluoromethyl-N-[2-(3-trifluoromethyl-phenyl)-ethyl]-benzamide | 524.2 [ISP(M + H)+] |
| B95 | 3,5-Dichloro-N-(4-cyclobutyl-benzyl)-N-[2-(3-trifluoromethyl-phenyl)-ethyl]-benzamide | 506.1 [ISP(M + H)+] |
| B96 | 3-Chloro-N-[2-(4-chloro-phenyl)-ethyl]-N-(4-cyclobutyl-benzyl)-2-fluoro-5-trifluoromethyl-benzamide | 524.2 [ISP(M + H)+] |
| B97 | 3-Chloro-N-[2-(4-chloro-phenyl)-ethyl]-N-(4-cyclobutyl-benzyl)-5-trifluoromethyl-benzamide | 506.2 [ISP(M + H)+] |
| B98 | N-[2-(4-Chloro-phenyl)-ethyl]-N-(4-cyclobutyl-benzyl)-3-fluoro-5-trifluoromethyl-benzamide | 490.3 [ISP(M + H)+] |
| B99 | 3,5-Dichloro-N-[2-(4-chloro-phenyl)-ethyl]-N-(4-cyclobutyl-benzyl)-benzamide | 472 [ISP(M + H)+] |
| B100 | 3-Chloro-N-(4-cyclobutyl-benzyl)-2-fluoro-N-[2-(4-fluoro-phenyl)-ethyl]-5-trifluoromethyl-benzamide | 508.4 [ISP(M + H)+] |
| B101 | 3-Chloro-N-(4-cyclobutyl-benzyl)-N-[2-(4-fluoro-phenyl)-ethyl]-5-trifluoromethyl-benzamide | 490.3 [ISP(M + H)+] |
| B102 | N-(4-Cyclobutyl-benzyl)-3-fluoro-N-[2-(4-fluoro-phenyl)-ethyl]-5-trifluoromethyl-benzamide | 474.1 [ISP(M + H)+] |
| B103 | 3,5-Dichloro-N-(4-cyclobutyl-benzyl)-N-[2-(4-fluoro-phenyl)-ethyl]-benzamide | 456.2 [ISP(M + H)+] |
| B104 | 3,5-Dichloro-N-[2-(4-chloro-phenyl)-ethyl]-N-[4-(1,2,2,2-tetrafluoro-1-trifluoromethyl-ethyl)-benzyl]-benzamide | 586.1 [ISP(M + H)+] |
| B105 | 3-Chloro-N-[2-(4-chloro-phenyl)-ethyl]-N-[4-(1,2,2,2-tetrafluoro-1-trifluoromethyl-ethyl)-benzyl]-5-trifluoromethyl-benzamide | 620.2 [ISP(M + H)+] |
| B106 | 3-Chloro-N-[2-(4-chloro-phenyl)-ethyl]-N-[4-(1,1-dimethyl-propyl)-benzyl]-2-fluoro-5-trifluoromethyl-benzamide | 540.3 [ISP(M + H)+] |

-continued

| Example | Name | MS |
|---|---|---|
| B107 | 3-Chloro-N-[2-(4-chloro-phenyl)-ethyl]-N-[4-(1,1-dimethyl-propyl)-benzyl]-5-trifluoromethyl-benzamide | 522.2 [ISP(M + H)+] |
| B108 | 3,5-Dichloro-N-[2-(4-chloro-phenyl)-ethyl]-N-[4-(1,1-dimethyl-propyl)-benzyl]-benzamide | 488.1 [ISP(M + H)+] |
| B109 | 3-Chloro-2-fluoro-5-trifluoromethyl-N-[2-(3-trifluoromethyl-phenyl)-ethyl]-N-(4-trimethylsilanyl-benzyl)-benzamide | 576.4 [ISP(M + H)+] |
| B110 | 3-Chloro-N-[2-(4-chloro-phenyl)-ethyl]-2-fluoro-5-trifluoromethyl-N-(4-trimethylsilanyl-benzyl)-benzamide | 542.2 [ISP(M + H)+] |
| B111 | 3-Chloro-2-fluoro-N-[2-(4-fluoro-phenyl)-ethyl]-5-trifluoromethyl-N-(4-trimethylsilanyl-benzyl)-benzamide | 526.2 [ISP(M + H)+] |
| B112 | 3-Chloro-N-[2-(3,4-dichloro-phenyl)-ethyl]-2-fluoro-5-trifluoromethyl-N-(4-trimethylsilanyl-benzyl)-benzamide | 576.3 [ISP(M + H)+] |
| B113 | 3-Chloro-2-fluoro-N-[2-(3-trifluoromethoxy-phenyl)-ethyl]-5-trifluoromethyl-N-(4-trimethylsilanyl-benzyl)-benzamide | 592.3 [ISP(M + H)+] |
| B114 | 3-Chloro-2-fluoro-N-[2-(3-trifluoromethyl-phenyl)-ethyl]-N-(4-trimethylsilanyl-benzyl)-benzamide | 508.4 [ISP(M + H)+] |
| B115 | 3-Chloro-N-[2-(4-chloro-phenyl)-ethyl]-2-fluoro-N-(4-trimethylsilanyl-benzyl)-benzamide | 474.2 [ISP(M + H)+] |
| B116 | 3-Chloro-2-fluoro-N-[2-(4-fluoro-phenyl)-ethyl]-N-(4-trimethylsilanyl-benzyl)-benzamide | 458.4 [ISP(M + H)+] |
| B117 | 3-Chloro-N-[2-(3,4-dichloro-phenyl)-ethyl]-2-fluoro-N-(4-trimethylsilanyl-benzyl)-benzamide | 508.3 [ISP(M + H)+] |
| B118 | 5-Chloro-N-[2-(4-chloro-phenyl)-ethyl]-2-fluoro-N-(4-trimethylsilanyl-benzyl)-benzamide | 474.2 [ISP(M + H)+] |
| B119 | 3,5-Dichloro-N-[2-(3-trifluoromethyl-phenyl)-ethyl]-N-(4-trimethylsilanyl-benzyl)-benzamide | 524.4 [ISP(M + H)+] |
| B120 | 3,5-Dichloro-N-[2-(4-chloro-phenyl)-ethyl]-N-(4-trimethylsilanyl-benzyl)-benzamide | 490.2 [ISP(M + H)+] |
| B121 | 3,5-Dichloro-N-[2-(4-fluoro-phenyl)-ethyl]-N-(4-trimethylsilanyl-benzyl)-benzamide | 474.2 [ISP(M + H)+] |
| B122 | 3,5-Dichloro-N-[2-(3,4-dichloro-phenyl)-ethyl]-N-(4-trimethylsilanyl-benzyl)-benzamide | 526.2 [ISP(M + H)+] |
| B123 | 3-Chloro-N-[2-(4-chloro-phenyl)-ethyl]-5-trifluoromethyl-N-(4-trimethylsilanyl-benzyl)-benzamide | 524.4 [ISP(M + H)+] |
| B124 | 3-Chloro-N-[2-(4-fluoro-phenyl)-ethyl]-5-trifluoromethyl-N-(4-trimethylsilanyl-benzyl)-benzamide | 508.4 [ISP(M + H)+] |
| B125 | 3-Chloro-N-[2-(3,4-dichloro-phenyl)-ethyl]-5-trifluoromethyl-N-(4-trimethylsilanyl-benzyl)-benzamide | 558.1 [ISP(M + H)+] |
| B126 | 3-Chloro-N-[4-(1,1-dimethyl-propyl)-benzyl]-5-trifluoromethyl-N-[2-(3-trifluoromethyl-phenyl)-ethyl]-benzamide | 556.2 [ISP(M + H)+] |
| B127 | 3-Chloro-5-trifluoromethyl-N-[2-(3-trifluoromethyl-phenyl)-ethyl]-N-(4-trimethylsilanyl-benzyl)-benzamide | 558 [ISP(M + H)+] |
| B128 | 3-Chloro-N-(4-cyclopropyl-benzyl)-N-[2-(3,4-dichloro-phenyl)-ethyl]-5-trifluoromethyl-benzamide | 526.1 [ISP(M + H)+] |
| B129 | 3-Chloro-N-[2-(4-chloro-phenyl)-ethyl]-5-trifluoromethyl-N-(4-trifluoromethyl-benzyl)-benzamide | 520 [ISP(M + H)+] |
| B130 | 3-Chloro-N-[2-(4-chloro-phenyl)-ethyl]-N-(4-trifluoromethoxy-benzyl)-5-trifluoromethyl-benzamide | 536 [ISP(M + H)+] |
| B131 | 3-Chloro-N-[2-(4-chloro-phenyl)-ethyl]-N-[4-(1-fluoro-cyclobutyl)-benzyl]-5-trifluoromethyl-benzamide | 524.1 [ISP(M + H)+] |
| B132 | 3-Chloro-N-[4-(1-fluoro-cyclobutyl)-benzyl]-N-[2-(4-fluoro-phenyl)-ethyl]-5-trifluoromethyl-benzamide | 508.1 [ISP(M + H)+] |
| B133 | 3-Chloro-N-[2-(3-chloro-phenyl)-ethyl]-N-[4-(1-fluoro-cyclobutyl)-benzyl]-5-trifluoromethyl-benzamide | 524.1 [ISP(M + H)+] |
| B134 | 3-Chloro-N-[4-(1-fluoro-cyclobutyl)-benzyl]-5-trifluoromethyl-N-[2-(3-trifluoromethyl-phenyl)-ethyl]-benzamide | 558 [ISP(M + H)+] |
| B135 | 3-Chloro-N-[2-(4-chloro-phenyl)-ethyl]-2-fluoro-N-[4-(1-fluoro-cyclobutyl)-benzyl]-5-trifluoromethyl-benzamide | 542.2 [ISP(M + H)+] |

-continued

| Example | Name | MS |
|---|---|---|
| B136 | 3-Chloro-2-fluoro-N-[4-(1-fluoro-cyclobutyl)-benzyl]-N-[2-(4-fluoro-phenyl)-ethyl]-5-trifluoromethyl-benzamide | 526.2 [ISP(M + H)+] |
| B137 | 3-Chloro-N-[2-(3-chloro-phenyl)-ethyl]-2-fluoro-N-[4-(1-fluoro-cyclobutyl)-benzyl]-5-trifluoromethyl-benzamide | 542.2 [ISP(M + H)+] |
| B138 | 3-Chloro-2-fluoro-N-[4-(1-fluoro-cyclobutyl)-benzyl]-5-trifluoromethyl-N-[2-(3-trifluoromethyl-phenyl)-ethyl]-benzamide | 576.3 [ISP(M + H)+] |
| B139 | N-(4-tert-Butyl-benzyl)-2-chloro-N-[2-(3,5-dichloro-phenyl)-ethyl]-6-trifluoromethyl-isonicotinamide | 542 [EI(M)+] |
| B140 | N-(4-tert-Butyl-benzyl)-3-chloro-N-[2-(3,5-dichloro-phenyl)-ethyl]-5-trifluoromethyl-benzamide | 541 [EI(M)+] |
| B141 | N-(4-tert-Butyl-benzyl)-3-chloro-N-[2-(3,5-dichloro-phenyl)-ethyl]-2-fluoro-5-trifluoromethyl-benzamide | 560.2 [ISP(M + H)+] |
| B142 | N-(4-tert-Butyl-benzyl)-3-chloro-N-[2-(4-chloro-3-trifluoromethyl-phenyl)-ethyl]-2-fluoro-5-trifluoromethyl-benzamide | 593.1 [EI(M)+] |
| B143 | N-(4-tert-Butyl-benzyl)-3-chloro-N-[2-(4-chloro-3-trifluoromethyl-phenyl)-ethyl]-5-trifluoromethyl-benzamide | 575.1 [EI(M)+] |
| B144 | N-(4-tert-Butyl-benzyl)-3-chloro-N-[2-(3-chloro-5-fluoro-phenyl)-ethyl]-2-fluoro-5-trifluoromethyl-benzamide | 544.1 [ISP(M + H)+] |
| B145 | N-(4-tert-Butyl-benzyl)-3-chloro-N-[2-(3-chloro-5-fluoro-phenyl)-ethyl]-5-trifluoromethyl-benzamide | 526.2 [ISP(M + H)+] |
| B146 | N-(4-tert-Butyl-benzyl)-2-chloro-N-[2-(3-chloro-4-fluoro-phenyl)-ethyl]-6-trifluoromethyl-isonicotinamide | 527.0 [ISP(M + H)+] |
| B147 | N-(4-tert-Butyl-benzyl)-2-chloro-N-[2-(4-chloro-3-trifluoromethyl-phenyl)-ethyl]-6-trifluoromethyl-isonicotinamide | 576.2 [EI(M)+] |
| B148 | N-[2-(3,5-Bis-trifluoromethyl-phenyl)-ethyl]-N-(4-tert-butyl-benzyl)-3-chloro-2-fluoro-5-trifluoromethyl-benzamide | 627.2 [EI(M)+] |
| B149 | 6-Chloro-4-trifluoromethyl-pyridine-2-carboxylic acid (4-tert-butyl-benzyl)-[2-(3-trifluoromethyl-phenyl)-ethyl]-amide | 543 [ISP(M + H)+] |
| B150 | 6-Chloro-4-trifluoromethyl-pyridine-2-carboxylic acid (4-tert-butyl-benzyl)-[2-(3-fluoro-5-trifluoromethyl-phenyl)-ethyl]-amide | 561.2 [ISP(M + H)+] |
| B151 | 6-Chloro-4-trifluoromethyl-pyridine-2-carboxylic acid (4-tert-butyl-benzyl)-[2-(3,4-dichloro-phenyl)-ethyl]-amide | 543.1 [ISP(M + H)+] |
| B152 | 6-Chloro-4-trifluoromethyl-pyridine-2-carboxylic acid (4-tert-butyl-benzyl)-[2-(3-fluoro-4-trifluoromethyl-phenyl)-ethyl]-amide | 561.2 [ISP(M + H)+] |
| B153 | N-(4-tert-Butyl-benzyl)-3-chloro-N-[2-(3-cyclopropyl-4-fluoro-phenyl)-ethyl]-2-fluoro-5-trifluoromethyl-benzamide | 550.3 [ISP(M + H)+] |
| B154 | 6-Methyl-2-trifluoromethyl-pyrimidine-4-carboxylic acid (4-tert-butyl-benzyl)-[2-(3-trifluoromethyl-phenyl)-ethyl]-amide | 524.4 [ISP(M + H)+] |
| B155 | N-Butyl-N-(4-tert-butyl-benzyl)-3-chloro-2-fluoro-5-trifluoromethyl-benzamide | 444.4 [ISP(M + H)+] |
| B156 | N-Butyl-N-(4-tert-butyl-benzyl)-3-fluoro-5-trifluoromethyl-benzamide | 409.2 [EI(M)+] |
| B157 | N-Butyl-N-(4-tert-butyl-benzyl)-2-fluoro-5-trifluoromethyl-benzamide | 410.5 [ISP(M + H)+] |
| B158 | N-(4-tert-Butyl-benzyl)-2,3,5-trichloro-N-[2-(3-trifluoromethyl-phenyl)-ethyl]-benzamide | 542.0 [ISP(M + H)+] |
| B159 | N-(4-tert-Butyl-benzyl)-2,3,5-trichloro-N-[2-(3-fluoro-5-trifluoromethyl-phenyl)-ethyl]-benzamide | 561.9 [ISP(M + H)+] |
| B160 | N-(4-tert-Butyl-benzyl)-3-chloro-N-[2-(3-chloro-4-fluoro-phenyl)-ethyl]-5-trifluoromethyl-benzamide | 526.1 [ISP(M + H)+] |
| B161 | N-(4-tert-Butyl-benzyl)-3-chloro-N-[2-(3-chloro-4-fluoro-phenyl)-ethyl]-2-fluoro-5-trifluoromethyl-benzamide | 544.2 [ISP(M + H)+] |

-continued

| Example | Name | MS | |
|---|---|---|---|
| B162 | N-(4-tert-Butyl-benzyl)-3-chloro-N-[2-(4-chloro-3-fluoro-phenyl)-ethyl]-2-fluoro-5-trifluoromethyl-benzamide | 544.3 | [ISP(M + H)+] |
| B163 | N-[2-(3-Bromo-phenyl)-ethyl]-N-(4-tert-butyl-benzyl)-3-chloro-5-trifluoromethyl-benzamide | 554.1 | [ISP(M + H)+] |
| B164 | N-(4-tert-Butyl-benzyl)-3-chloro-N-[2-(3-ethyl-phenyl)-ethyl]-2-fluoro-5-trifluoromethyl-benzamide | 520.4 | [ISP(M + H)+] |
| B165 | N-(4-tert-Butylbenzyl)-3-chloro-N-[2-(3-cyclopropyl-4-fluorophenyl)-ethyl]-5-trifluoromethyl-benzamide | 532.3 | [ISP(M + H)+] |
| B166 | N-(4-tert-Butylbenzyl)-3-chloro-N-[2-(3,4-dicyclopropylphenyl)-ethyl]-2-fluoro-5-trifluoromethyl-benzamide | 572.3 | [ISP(M + H)+] |
| B167 | N-(4-tert-Butylbenzyl)-3-chloro-N-[2-(4-chloro-3-cyclopropylphenyl)-ethyl]-2-fluoro-5-trifluoromethyl-benzamide | 566.2 | [ISP(M + H)+] |
| B168 | N-(4-tert-Butylbenzyl)-3-chloro-N-[2-(4-chloro-3-isopropylphenyl)-ethyl]-5-trifluoromethyl-benzamide | 550.4 | [ISP(M + H)+] |
| B169 | N-(4-tert-Butylbenzyl)-3-chloro-N-[2-(4-chloro-3-isopropylphenyl)-ethyl]-2-fluoro-5-trifluoromethyl-benzamide | 568.2 | [ISP(M + H)+] |
| B170 | N-(4-tert-Butyl-benzyl)-3-chloro-2-fluoro-5-trifluoromethyl-N-[3-(3-trifluoromethyl-phenyl)-propyl]-benzamide | 574.4 | [ISP(M + H)+] |
| B171 | N-(4-tert-Butyl-benzyl)-3-chloro-N-[2-(4-chloro-3-ethyl-phenyl)-ethyl]-2-fluoro-5-trifluoromethyl-benzamide | 554.3 | [ISP(M + H)+] |
| B172 | N-(4-tert-Butyl-benzyl)-3-chloro-N-[3-(3-chloro-phenyl)-propyl]-2-fluoro-5-trifluoromethyl-benzamide | 540.3 | [ISP(M + H)+] |
| B173 | N-(4-tert-Butyl-benzyl)-3-chloro-N-[3-(3-chloro-phenyl)-propyl]-5-trifluoromethyl-benzamide | 522.2 | [ISP(M + H)+] |
| B174 | N-(4-tert-Butyl-benzyl)-3-chloro-N-[3-(4-chloro-phenyl)-propyl]-2-fluoro-5-trifluoromethyl-benzamide | 540.3 | [ISP(M + H)+] |
| B175 | N-(4-tert-Butyl-benzyl)-3-chloro-N-[3-(4-chloro-phenyl)-propyl]-5-trifluoromethyl-benzamide | 522.2 | [ISP(M + H)+] |
| B176 | 3-Bromo-N-(4-tert-butyl-benzyl)-5-chloro-N-[2-(3-trifluoromethyl-phenyl)-ethyl]-benzamide | 552 | [ISP(M + H)+] |
| B177 | 3-Bromo-N-(4-tert-butyl-benzyl)-5-chloro-N-[2-(3-fluoro-5-trifluoromethyl-phenyl)-ethyl]-benzamide | 570.3 | [ISP(M + H)+] |
| B178 | N-[2-(3-Bromo-4-fluoro-phenyl)-ethyl]-N-(4-tert-butyl-benzyl)-3-chloro-2-fluoro-5-trifluoromethyl-benzamide | 590.3 | [ISP(M + H)+] |

EXAMPLE 2

N-(4-tert-butyl-benzyl)-3-chloro-2-fluoro-N-[2-(3-hydroxy-phenyl)-ethyl]-5-trifluoromethyl-benzamide a) Preparation of N-[2-(3-benzyloxy-phenyl)-ethyl]-N-(4-tert-butyl-benzyl)-3-chloro-2-fluoro-5-trifluoromethyl-benzamide The title compound was prepared in analogy to Example 1, using [2-(3-benzyloxy-phenyl)-ethyl]-(4-tert-butyl-benzyl)-amine (S9-C43) and 3-chloro-2-fluoro-5-(trifluoromethyl) benzoic acid. MS: 597.3 [ISP (M+H)+].

b) Preparation of N-(4-tert-butyl-benzyl)-3-chloro-2-fluoro-N-[2-(3-hydroxy-phenyl)-ethyl]-5-trifluoromethyl-benzamide A solution of 1.1 g of N-[2-(3-benzyloxy-phenyl)-ethyl]-N-(4-tert-butyl-benzyl)-3-chloro-2-fluoro-5-trifluoromethyl-benzamide (1.84 mmol) in 50 ml ethyl acetate was hydrogenated over 0.33 g Pd/C-5%. After completion of the reaction the suspension was filtered off and concentrated in vacuo to give 0.75 g of a colorless amorphous material. MS: 508.4 [ISP (M+H)+].

EXAMPLE 3

N-(4-tert-butyl-benzyl)-3-chloro-5-ethyl-N-[2-(3-fluoro-5-trifluoromethyl-phenyl)-ethyl]-benzamide 285 mg of 3-bromo-N-(4-tert-butyl-benzyl)-5-chloro-N-[2-(3-fluoro-5-trifluoromethyl-phenyl)-ethyl]-benzamide (0.6 mmol, Example B177), 44 mg of ethylboronic acid (1.75 mmol), 371 mg of tri-potassium phosphate (0.05 mmol), 14 mg of tricyclohexylphosphine and 6 mg of palladium acetate were suspended in 2.3 ml toluene and 0.1 ml water and stirred at 100° C. for 3.5 h under nitrogen. The reaction mixture was then cooled down to RT, diluted with 4 ml water and extracted twice with ethylacetate. The combined organic layers were washed with brine, dried over magnesium sulfate, filtered off and concentrated under vacuo. The resulting residue was purified by flash column chromatography (Heptane/AcOEt: 95/5) to yield 192 mg of a yellow solid. MS (ISP) 520.3 (M+H)+.

EXAMPLE 3-b

N-(4-tert-butyl-benzyl)-3-chloro-5-ethyl-N-[2-(3-trifluoromethyl-phenyl)-ethyl]-benzamide The title compound was prepared in analogy to Example 3, using 3-bromo-N-(4-tert-butyl-benzyl)-5-chloro-N-[2-(3-trifluoromethyl-phenyl)-ethyl]-benzamide (Example B176). MS (ISP) 502.3 (M+H)+.

EXAMPLE 3-c

N-(4-tert-butyl-benzyl)-3-ethyl-2-fluoro-N-[2-(3-fluoro-5-trifluoromethyl-phenyl)-ethyl]-5-trifluoromethyl-benzamide The title compound was prepared in analogy to example 3, using N-(4-tert-butyl-benzyl)-3-chloro-2-fluoro-N-[2-(3-fluoro-5-trifluoromethyl-phenyl)-ethyl]-5-trifluoromethyl-benzamide (Example B63). MS (ISP) 572.3 (M+H)$^+$.

EXAMPLE 3-d

N-(4-tert-butyl-benzyl)-2-fluoro-N-[2-(3-fluoro-5-trifluoromethyl-phenyl)-ethyl]-5-trifluoromethyl-benzamide The title compound was prepared in analogy to example 3, using N-(4-tert-butyl-benzyl)-3-chloro-2-fluoro-N-[2-(3-fluoro-5-trifluoromethyl-phenyl)-ethyl]-5-trifluoromethyl-benzamide (Example B63). 544.2 [ISP (M+H)$^+$]

EXAMPLE 3-e

N-(4-tert-butyl-benzyl)-3-chloro-5-propyl-N-[2-(3-trifluoromethyl-phenyl)-ethyl]-benzamide The title compound was prepared in analogy to example 3, using 3-bromo-N-(4-tert-butyl-benzyl)-5-chloro-N-[2-(3-trifluoromethyl-phenyl)-ethyl]-benzamide (Example B176) and n-propylboronic acid. 516.2 [ISP (M+H)$^+$]

EXAMPLE 3-f

N-(4-tert-butyl-benzyl)-3-chloro-N-[2-(3-fluoro-5-trifluoromethyl-phenyl)-ethyl]-5-propyl-benzamide The title compound was prepared in analogy to example 3, using 3-bromo-N-(4-tert-butyl-benzyl)-5-chloro-N-[2-(3-fluoro-5-trifluoromethyl-phenyl)-ethyl]-benzamide (Example B177) and n-propylboronic acid. 534.3 [ISP (M+H)$^+$]

EXAMPLE 3-g

N-(4-tert-butyl-benzyl)-3-chloro-N-[2-(3-ethyl-4-fluoro-phenyl)-ethyl]-2-fluoro-5-trifluoromethyl-benzamide The title compound was prepared in analogy to example 3, using N-[2-(3-bromo-4-fluoro-phenyl)-ethyl]-N-(4-tert-butyl-benzyl)-3-chloro-2-fluoro-5-trifluoromethyl-benzamide (Example B178) and ethylboronic acid. 538.3 [ISP (M+H)$^+$]

EXAMPLE 3-h

N-(4-tert-butyl-benzyl)-3-chloro-2-fluoro-N-[2-(4-fluoro-3-propyl-phenyl)-ethyl]-5-trifluoromethyl-benzamide The title compound was prepared in analogy to example 3, using N-[2-(3-bromo-4-fluoro-phenyl)-ethyl]-N-(4-tert-butyl-benzyl)-3-chloro-2-fluoro-5-trifluoromethyl-benzamide (Example B178) and n-propylboronic acid. 552.2 [ISP (M+H)$^+$]

EXAMPLE 4

N-(4-tert-butyl-benzyl)-N-[2-(3-tert-butyl-4-hydroxy-phenyl)-ethyl]-3-chloro-2-fluoro-5-trifluoromethyl-benzamide a) Preparation of N-[2-(4-benzyloxy-3-tert-butyl-phenyl)-ethyl]-N-(4-tert-butyl-benzyl)-3-chloro-2-fluoro-5-trifluoromethyl-benzamide The title compound was prepared in analogy to Example 1, using [2-(4-benzyloxy-3-tert-butyl-phenyl)-ethyl]-(4-tert-butyl-benzyl)-amine (S9-C48) and 3-chloro-2-fluoro-5-(trifluoromethyl)benzoic acid. MS: 654.4 [ISP (M+H)$^+$].

b) Preparation of N-(4-tert-butyl-benzyl)-N-[2-(3-tert-butyl-4-hydroxy-phenyl)-ethyl]-3-chloro-2-fluoro-5-trifluoromethyl-benzamide A solution of 182 mg of N-[2-(4-benzyloxy-3-tert-butyl-phenyl)-ethyl]-N-(4-tert-butyl-benzyl)-3-chloro-2-fluoro-5-trifluoromethyl-benzamide (0.278 mmol) in 15 ml ethyl acetate were hydrogenated over 100 mg Pd/C-5%. After completion of the reaction the suspension was filtered off and concentrated in vacuo. The resulting residue was purified by flash column chromatography (Heptane/AcOEt:90/10) to yield 130 mg of a colorless viscous oil. MS (ISP) 564 (M+H)$^+$.

The compounds of formula I are cholesteryl ester transfer protein (CETP) inhibitors.

Atherosclerosis and its associated coronary heart disease is the leading cause of death in the industrialized world. Risk for development of coronary heart disease has been shown to be strongly correlated with certain plasma lipid levels. Lipids are transported in the blood by lipoproteins. The general structure of lipoproteins is a core of neutral lipids (triglyceride and cholesterol ester) and an envelope of polar lipids (phospholipids and non esterified cholesterol). There are three different classes of plasma lipoproteins with different core lipid content: the low density lipoprotein (LDL) which is cholesteryl ester (CE) rich; high density lipoprotein (HDL) which is also cholesteryl ester (CE) rich; and the very low density lipoprotein (VLDL) which is triglyceride (TG) rich. The different lipoproteins can be separated based on their different flotation density or size.

High LDL-cholesterol (LDL-C) and triglyceride levels are positively correlated, while high levels of HDL-cholesterol (HDL-C) are negatively correlated with the risk for developing cardiovascular diseases.

Plasma lipoprotein metabolism can be described as a flux of cholesterol between liver and the other tissues. The LDL pathway corresponds to the secretion of VLDL from the liver to deliver cholesterol by LDL to tissues. Any alteration in LDL catabolism could lead to uptake of excess cholesterol in the vessel wall forming foam cells and atherosclerosis. The opposite pathway is the mobilization of free cholesterol from peripheral tissues by HDL to deliver cholesterol to the liver to be eventually excreted with bile. In humans a significant part of cholesteryl ester (CE) is transferred from HDL to the VLDL, LDL pathway. This transfer is mediated by a 70,000 dalton plasma glycoprotein, the cholesteryl ester transfer protein (CETP).

Mutations in the CETP gene associated with CETP deficiency are characterized by high HDL-cholesterol levels (>60 mg/dL) and reduced cardiovascular risk. Such findings are consistent with studies of pharmacologically mediated inhibition of CETP in the rabbit, which argue strongly in favor of CETP inhibition as a valid therapeutic approach [Le Goff et al., Pharmacology & Therapeutics 101:17-38 (2004); Okamoto et al., Nature 406:203-207 2000)].

No wholly satisfactory HDL-elevating therapies exist. Niacin can significantly increase HDL, but has serious toleration issues which reduce compliance. Fibrates and the HMG CoA reductase inhibitors raise HDL-cholesterol only modestly (–10-12%). As a result, there is a significant unmet medical need for a well tolerated agent which can significantly elevate plasma HDL levels. The net result of CETP activity is a lowering of HDL-C and an increase in LDL-C. This effect on lipoprotein profile is believed to be pro-atherogenic, especially in subjects whose lipid profile constitutes an increased risk for coronary heart disease. Therefore by inhibiting CETP activity there is the potential to inverse this relationship towards a lower risk and ultimately to protect against coronary heart diseases and associated mortality.

Thus, CETP inhibitors are useful as medicaments for the treatment and/or prophylaxis of atherosclerosis, peripheral vascular disease, dyslipidemia, hyperbeta-lipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

In addition, CETP inhibitors may be used in combination with another compound, said compound being an HMG-CoA reductase inhibitor, a microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant.

As described above, the compounds of formula I of the present invention can be used as medicaments for the treatment and/or prophylaxis of diseases which are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. The use as medicament for the treatment and/or prevention of dyslipidemia is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prophylaxis of diseases which are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia.

In another embodiment, the invention relates to a method for the treatment and/or prophylaxis of diseases which are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. A method for the treatment and/or prophylaxis of dyslipidemia is preferred. The invention further relates to the use of compounds of formula I as defined above for the treatment and/or prophylaxis of diseases are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. The use of compounds of formula I as defined above for the treatment and/or prophylaxis of dyslipidemia is preferred.

In addition, the invention relates to the use of compounds of formula I as defined above for the preparation of medicaments for the treatment and/or prophylaxis of diseases are mediated by CETP. Examples of such diseases are atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia. The use of compounds of formula I as defined above for the preparation of medicaments for the treatment and/or prophylaxis of dyslipidemia is preferred.

In addition, CETP inhibitors are useful in combination with another compound, said compound being an HMG-CoA reductase inhibitor, an microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant.

The invention therefore also relates to pharmaceutical compositions comprising a compound of formula I as defined above in combination with an HMG-CoA reductase inhibitor, an microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant, as well as a pharmaceutically acceptable carrier and/or adjuvant.

The invention further relates to the use of compounds of formula I as defined above in combination with an HMG-CoA reductase inhibitor, a microsomal triglyceride transfer protein (MTP)/ApoB secretion inhibitor, a PPAR activator, a bile acid reuptake inhibitor, a cholesterol absorption inhibitor, a cholesterol synthesis inhibitor, a fibrate, niacin, an ion-exchange resin, an antioxidant, an ACAT inhibitor or a bile acid sequestrant for the treatment and/or prophylaxis of diseases such as atherosclerosis, peripheral vascular disease, dyslipidemia, hyperbetalipoproteinemia, hypoalphalipoproteinemia, hypercholesterolemia, hypertriglyceridemia, familial hypercholesterolemia, cardiovascular disorders, angina, ischemia, cardiac ischemia, stroke, myocardial infarction, reperfusion injury, angioplastic restenosis, hypertension, and vascular complications of diabetes, obesity or endotoxemia, as well as to the use of such a combination for the preparation of corresponding medicaments.

The compounds of formula I and their pharmaceutically acceptable salts possess valuable pharmacological properties. Specifically, it has been found that the compounds of the present invention are inhibitors of the cholesteryl ester transfer protein (CETP).

The following tests were carried out in order to determine the activity of the compounds of formula I.

Activity of CETP inhibitors was determined using a buffer assay system. Partially purified CETP transferred radiolabeled cholesteryl ester from HDL donor particles to biotin-labeled LDL acceptor particles. The reaction was stopped by addition of streptavidin-coupled scintillation proximity assay (SPA) beads. These beads captured the biotinylated acceptor particles and transferred radioactivity was measured. The assay system was purchased and performed according to manufacturer's recommendations (Amersham Biosciences). Inhibitory activity of compounds was determined as percentage of positive control activity containing CETP together with donor and acceptor particles. Serial dilution of compounds was performed in order to determine the $IC_{50}$ values.

Activity of the compounds was subsequently measured in the presence of plasma using the same assay as described above except that the source of CETP was human lipoprotein-deprived serum (LPDS). Inhibitory activity of compounds was determined as percentage of positive control activity containing all the assay components except compound. Serial dilution of compounds was performed in order to determine the $IC_{50}$ values.

Under the latter assay conditions, the compounds of the present invention exhibit $IC_{50}$ values within the range of about 1 nM to about 100 μM, e.g., of about 1 nM to about 1 μM, e.g., of about 1 nM to about 200 nM. The following table shows measured values for some selected compounds of the present invention.

|  | $IC_{50}$ (nM) |
| --- | --- |
| Compound B3 | 66848 |
| Compound B104 | 1248 |
| Compound B108 | 409 |

In vivo activity of the compounds of formula I were determined in hamster using the following protocol:

Male golden Syrian hamsters (6-week-old, 100-130 g) under standard chow diet received compounds in the morning by oral gavage using appropriate vehicle, blood was taken 2 h later by retro-orbital bleeding under isofluran anaesthesia and 7 h later on sacrificed animals. Plasma was separated from blood using low speed centrifugation and CETP activity was measured in plasma using the radioactive CETP activity assay as described above except that diluted plasma replaced LPDS. In vivo CETP inhibition was expressed as CETP activity remaining in the plasma of treated animals as compared to plasma CETP activity of placebo treated animals.

Efficacy of compounds in modulating plasma lipid levels can be determined in hamsters after 7 days of daily administration of compounds. Male hamsters are acclimated for 3-4 days to receive food as a paste made of 10 g chow and 10 g water per day. Compounds are then mixed within this paste and a portion containing the proper amount of compounds is given every morning for 7 days. Alternatively compounds can be given by oral gavage using the proper vehicle. Blood is taken before compound treatment by retro-orbital bleeding and at the end of the treatment on sacrificed animals. Plasma is separated from blood by low speed centrifugation and selected organs are taken (e.g liver, fat, brain, etc.). Effects of compounds on plasma lipid levels are determined by measuring total cholesterol, HDL-cholesterol, LDL-cholesterol and triglyceride using calorimetric enzymatic assays (Roche Diagnostic GmbH, Mannheim, Germany). HDL-C, LDL-C and VLDL-C are e.g., quantified using size exclusion chromatography on superpose-6 column using SMART™ system (Pharmacia). Lipoprotein distribution is calculated assuming a Gaussian distribution for each peak, using a non-linear, least-squares curve-fitting procedure to calculate the area under the curve. Plasma samples are also used to quantify CETP activity as described above. Compound concentration is also determined in plasma and selected tissues as liver, fat, heart, muscle and brain.

Efficacy of compounds in modulating plasma lipid levels was also determined in cholesterol/fat fed hamsters. The protocol is identical as described above except that animals are fed with chow diet enriched with 10% (w/w) saturated fat and 0.05% (w/w) cholesterol. Animals received this high fat diet 2 weeks before starting compound administration and continued this diet throughout the study. The 2 weeks pre-treatment induced an increase in plasma cholesterol and triglyceride levels allowing a better assessment of LDL-C and triglyceride lowering.

Efficacy of compounds in its ability to acutely raise HDL-C can be assessed in cynomolgus monkeys. Animals are fed with standard primate maintenance diet. Compounds are formulated with appropriate vehicle and administered to animals by oral gavage. Blood is taken before and at several time-points after compound administration (usually 30 min, 1 h, 2 h, 4 h, 7 h and 24 h). Plasma is separated from blood by low speed centrifugation and CETP activity and plasma lipids are quantified. Compound potency and efficacy can be assessed by measuring the HDL-C increase after this single-dose administration. In such pharmacodynamic model the extent together with the kinetics of the pharmacologic effect can be assessed.

The compounds of formula I and their pharmaceutically acceptable salts and esters can be used as medicaments, e.g. in the form of pharmaceutical preparations for enteral, parenteral or topical administration. They can be administered, e.g., perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, e.g., lactose, corn starch or derivatives thereof, talc, stearic acid or its salts can be used as carrier materials for tablets, coated tablets, dragées and hard gelatine capsules. Suitable carrier materials for soft gelatine capsules are, e.g., vegetable oils, waxes, fats and semi-solid and liquid polyols (depending on the nature of the active ingredient no carriers are, however, required in the case of soft gelatine capsules). Suitable carrier materials for the production of solutions and syrups are, e.g., water, polyols, sucrose, invert sugar and the like. Suitable carrier materials for injection solutions are, e.g., water, alcohols, polyols, glycerol and vegetable oils. Suitable carrier materials for suppositories are, e.g., natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, e.g., 0.5-100 mg, of a compound of formula I.

The following examples serve to illustrate the present invention in more detail. They are, however, not intended to limit its scope in any manner.

EXAMPLE A

Film Coated Tablets

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magnesium stearate and compressed to yield kernels of 120 or 350 mg respectively. The kernels are lacquered with an aqueous solution/suspension of the above mentioned film coat.

EXAMPLE B

Capsules

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

EXAMPLE C

Injection Solutions

| | |
|---|---|
| Compound of formula (I) | 3.0 mg |
| Gelatin | 150.0 mg |
| Phenol | 4.7 mg |
| Sodium carbonate | to obtain a final pH of 7 |
| Water for injection solutions | ad 1.0 ml |

EXAMPLE D

Soft Gelatin Capsules

| | |
|---|---|
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

The invention claimed is:

1. A compound of formula I:

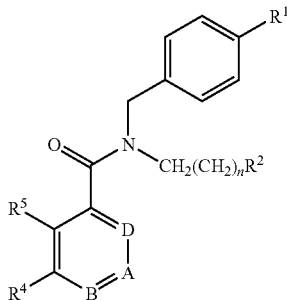
(I)

or pharmaceutically acceptable salts thereof, wherein:
$R^1$ is $C_1$-$C_6$alkyl, halo-$C_1$-$C_6$alkyl, halo-$C_1$-$C_6$alkoxy, $C_3$-$C_8$cycloalkyl, halo-$C_3$-$C_8$cycloalkyl or tri-$C_1$-$C_6$alkylsilyl;
$R^2$ is a group:

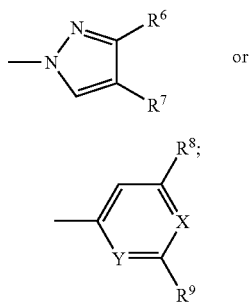

wherein:
$R^6$ and $R^7$ are independently hydrogen, $C_1$-$C_6$alkyl, halo-$C_1$-$C_6$alkyl, halogen, $C_3$-$C_8$cycloalkyl, OH or halo-$C_1$-$C_6$alkoxy;
$R^8$ and $R^9$ are independently hydrogen, $C_1$-$C_6$alkyl, halo-$C_1$-$C_6$alkyl, halogen, $C_3$-$C_8$cycloalkyl, OH or halo-$C_1$-$C_6$alkoxy;
X is $CR^{12}$;
Y is CH;
$R^{12}$ is halo-$C_1$-$C_6$alkyl, halogen, $C_3$-$C_8$cycloalkyl, OH or halo-$C_1$-$C_6$alkoxy;
$R^5$ is halo-$C_1$-$C_6$alkyl, halogen, $C_3$-$C_8$cycloalkyl, OH or halo-$C_1$-$C_6$alkoxy;
$R^4$ is hydrogen, $C_1$-$C_6$alkyl, halo-$C_1$-$C_6$alkyl, halogen, $C_3$-$C_8$cycloalkyl, OH or halo-$C_1$-$C_6$alkoxy;
A is $CR^{10}$ or N; wherein $R^{10}$ is hydrogen, $C_1$-$C_6$alkyl, halo-$C_1$-$C_6$alkyl, halogen, $C_3$-$C_8$cycloalkyl, OH or halo-$C_1$-$C_6$alkoxy;
B is $CR^{11}$ or N; wherein $R^{11}$ is hydrogen; or $R^{11}$ is $C_1$-$C_6$alkyl, halo-$C_1$-$C_6$alkyl, halogen, $C_3$-$C_8$cycloalkyl, OH or halo-$C_1$-$C_6$alkoxy, when at least two of $R^3$, $R^4$, $R^5$ and $R^{10}$ are not hydrogen;
D is $CR^3$ or N; wherein $R^3$ is hydrogen, $C_1$-$C_6$alkyl, halo-$C_1$-$C_6$alkyl, halogen, $C_3$-$C_8$cycloalkyl, OH or halo-$C_1$-$C_6$alkoxy;
wherein -B=A- and -A=D- are not —N=N—; and at least two of $R^3$, $R^4$, $R^5$, $R^{10}$ and $R^{11}$ are not hydrogen; and
n is 1, 2 or 3.

2. A compound according to claim 1 wherein $R^1$ is $C_1$-$C_6$alkyl, halo-$C_1$-$C_6$alkyl, $C_3$-$C_8$cycloalkyl, halo-$C_3$-$C_8$cycloalkyl or tri-$C_1$-$C_6$alkylsilyl.

3. A compound according to claim 1 wherein $R^2$ is a group (a).

4. A compound according to claim 1 wherein $R^2$ is a group (b).

5. A compound according to claim 1 wherein A is $CR^{10}$.

6. A compound according to claim 1 wherein:
A is N;
B is $CR^{11}$; and
D is $CR^3$.

7. A compound according to claim 1 wherein:
A is $CR^{10}$;
B is $CR^{11}$ or N; and
D is $CR^3$.

8. A compound according to claim 1 wherein:
$R^1$ is $C_1$-$C_6$alkyl;
$R^2$ is a group:

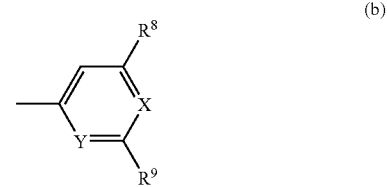
(b)

wherein:
$R^8$ and $R^9$ are independently hydrogen, halo-$C_1$-$C_6$alkyl, halogen, $C_3$-$C_8$cycloalkyl or halo-$C_1$-$C_6$alkoxy;
X is $CR^{12}$, wherein $R^{12}$ is halogen or $C_3$-$C_8$cycloalkyl; and Y is CH;
$R^5$ is halogen;
$R^4$ is $C_1$-$C_6$alkyl, halo-$C_1$-$C_6$alkyl or halogen;
A is $CR^{10}$;
B is $CR^{11}$ or N;
D is $CR^3$;
$R^3$ is hydrogen;
$R^{10}$ is halo-$C_1$-$C_6$alkyl or halogen; and
$R^{11}$ is hydrogen.

9. A compound of claim 5 wherein $R^2$ is

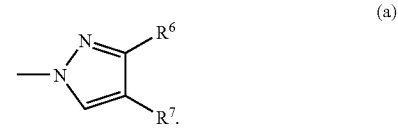
(a)

10. A compound of claim 5 wherein $R^2$ is

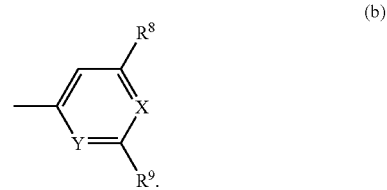
(b)

11. A compound of claim 6 wherein $R^2$ is

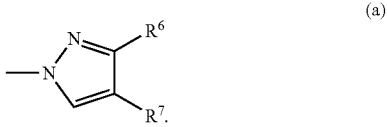
(a)

12. A compound of claim 6 wherein $R^2$ is

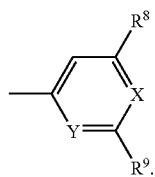
(b)

13. A compound of claim 7 wherein $R^2$ is

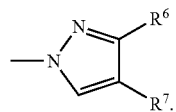
(a)

14. A compound of claim 7 wherein $R^2$ is

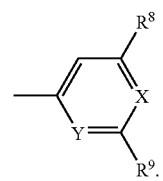
(b)

15. A pharmaceutical composition comprising a compound according to claim 1 and a pharmaceutically acceptable carrier or adjuvant or mixture thereof.

16. N-(4-tert-Butyl-benzyl)-3-chloro-N-[2-(4-chloro-3-ethyl-phenyl)-ethyl]-2-fluoro-5-trifluoromethyl-benzamide or a pharmaceutically acceptable salt thereof.

17. N-(4-tert-Butyl-benzyl)-3-chloro-N-[2-(4-chloro-3-ethyl-phenyl)-ethyl]-2-fluoro-5-trifluoromethyl-benzamide.

* * * * *

UNITED STATES PATENT AND TRADEMARK OFFICE
CERTIFICATE OF CORRECTION

| | | |
|---|---|---|
| PATENT NO. | : 7,745,477 B2 | Page 1 of 1 |
| APPLICATION NO. | : 11/698221 | |
| DATED | : June 29, 2010 | |
| INVENTOR(S) | : Conte et al. | |

It is certified that error appears in the above-identified patent and that said Letters Patent is hereby corrected as shown below:

Claim 1, column 55, delete line 16
and insert -- or a pharmaceutically acceptable salt thereof, wherein: --

Signed and Sealed this

Fourteenth Day of September, 2010

David J. Kappos
*Director of the United States Patent and Trademark Office*